United States Patent
Hu

(10) Patent No.: US 8,962,307 B2
(45) Date of Patent: Feb. 24, 2015

(54) METHOD AND KIT FOR DIAGNOSING AUTISM USING GENE EXPRESSION PROFILING

(75) Inventor: Valerie Wailin Hu, Rockville, MD (US)

(73) Assignee: The George Washington University, Washington, DC (US)

( * ) Notice: Subject to any disclaimer, the term of this patent is extended or adjusted under 35 U.S.C. 154(b) by 0 days.

(21) Appl. No.: 13/114,801

(22) Filed: May 24, 2011

(65) Prior Publication Data

US 2012/0015838 A1    Jan. 19, 2012

Related U.S. Application Data

(63) Continuation of application No. 12/107,046, filed on Apr. 21, 2008, now abandoned, which is a continuation of application No. 11/733,162, filed on Apr. 9, 2007, now abandoned.

(51) Int. Cl.
   *C12Q 1/68*    (2006.01)
(52) U.S. Cl.
   CPC ........ *C12Q 1/6883* (2013.01); *C12Q 2600/158* (2013.01); *C12Q 2600/112* (2013.01); *C12Q 2600/136* (2013.01)
   USPC ...................................... 435/287.2; 536/24.3
(58) Field of Classification Search
   None
   See application file for complete search history.

(56) References Cited

U.S. PATENT DOCUMENTS

| | | | |
|---|---|---|---|
| 5,578,832 | A | 11/1996 | Trulson et al. |
| 6,395,482 | B1 | 5/2002 | Karayiorgou et al. |
| 6,964,850 | B2 | 11/2005 | Bevilacqua et al. |
| 6,979,542 | B2 | 12/2005 | Cheung et al. |
| 2001/0051344 | A1* | 12/2001 | Shalon et al. ............. 435/6 |
| 2005/0084880 | A1 | 4/2005 | Duman et al. |
| 2008/0171715 | A1 | 7/2008 | Brown et al. |
| 2009/0053706 | A1 | 2/2009 | Laird et al. |
| 2009/0117562 | A1 | 5/2009 | Hu |
| 2009/0253583 | A1 | 10/2009 | Yoganathan |
| 2010/0029009 | A1 | 2/2010 | Stevenson et al. |
| 2010/0233662 | A1 | 9/2010 | Casper |
| 2011/0166029 | A1 | 7/2011 | Margulies et al. |

FOREIGN PATENT DOCUMENTS

WO    WO 2010/056982 A2    5/2010

OTHER PUBLICATIONS

Lee (Clinical Chemistry, 47:8, 1350-1352 (2001).*
Michiels et al. Lancet, 2005; 365:488-492.*
Slonin, Nature Genetics Supplement, vol. 32, Dec. 2002, pp. 502-508.*
Baker. Journal of the National Cancer Institute, vol. 95, No. 7, Apr. 2, 2003, pp. 511-515.*
Cheung et al (2003) Nature Genetics vol. 22 pp. 422-425.*
Thisted (1998) What is a P-value? obtained from http://www.stat.uchicago.edu/~thisted Six pages.*
Baron et al. 2006 J Autism Dev Disord 36:973-982.*
Gregg et al. 2008 Genomics 91:22-29.*
Nishimura et al. 2007. Human Molecular Genetics, 2007, vol. 16, No. 14 pp. 1682-1698.*
Temple University. DNA Microarray Facility website. Copyright 2003, Temple University. Three pages. Obtained from http://replay.waybackmachine.org/20060523221405/http://www.temple.edu/ovpr/ovpr/sh . . . Nov. 15, 2010.*
Traynor et al. BMC Medical Genetics 2002, 3:12, fifteen pages.*
Search results for query: slc6a4 from https://www.affymetrix.com/analysis/netaffx/showresults.affx accessed [Aug. 15, 2012].*
Search results for query: robo1 from https://www.affymetrix.com/analysis/netaffx/showresults.affx accessed [Aug. 15, 2012].*
Search results for query: alox5ap from https://www.affymetrix.com/analysis/netaffx/showresults.affx accessed [Aug. 15, 2012].*
Search results for query: ass from https://www.affymetrix.com/analysis/netaffx/showresults.affx accessed [Aug. 15, 2012].*
Search results for query: chl1 from https://www.affymetrix.com/analysis/netaffx/showresults.affx accessed [Aug. 15, 2012].*
Search results for query: dapk1 from https://www.affymetrix.com/analysis/netaffx/showresults.affx accessed [Aug. 15, 2012].*
Search results for query: egr2 from https://www.affymetrix.com/analysis/netaffx/showresults.affx accessed [Aug. 15, 2012].*
Search results for query: il6st from https://www.affymetrix.com/analysis/netaffx/showresults.affx accessed [Aug. 15, 2012].*
Search results for query: itgb7 from https://www.affymetrix.com/analysis/netaffx/showresults.affx accessed [Aug. 15, 2012].*
Kakiuchi et al. Nature Genetics vol. 32, No. 2, Oct. 2003, pp. 171-175.*
Mak et al. BMC Genetics 2004, vol. 5. This article is available from: http://www.biomedcentral.com/1471-2156/5/14; eight pages.*
Tang et al. Ann Neurol 2004;56:808-814, included also two supplemental data tables.*
Baron et al. J Autism Dev Disord (2006) 36:973-982.*
Search results for query: ROBO1 https://www.affymetrix.com/analysis/netaffx/showresults.affx accessed Jul. 24, 2014, one page.*
Search results for query: "il6st" https://www.affymetrix.com/analysis/netaffx/showresults.affx accessed Jul. 24, 2014, one page.*
Search results for query: CHL1 https://www.affymetrix.com/analysis/netaffx/showresults.affx accessed Jul. 24, 2014, one page.*
Search results for query: ALOX5AP https://www.affymetrix.com/analysis/netaffx/showresults.affx accessed Jul. 24, 2014, one page.*
Search results for query: DAPK1 https://www.affymetrix.com/analysis/netaffx/showresults.affx accessed Jul. 24, 2014, one page.*
Search results for query: ITGB7 https://www.affymetrix.com/analysis/netaffx/showresults.affx accessed Jul. 24, 2014, one page.*
Search results for query: SLC6A4 https://www.affymetrix.com/analysis/netaffx/showresults.affx accessed Jul. 24, 2014, one page.*
Search results for query: ASS https://www.affymetrix.com/analysis/netaffx/showresults.affx accessed Jul. 24, 2014, one page.*

(Continued)

*Primary Examiner* — Juliet Switzer
(74) *Attorney, Agent, or Firm* — Crowell & Moring LLP

(57) ABSTRACT

This invention relates to DNA microarray technology, and more specifically to methods and kits for identifying autism and autism spectrum disorders in humans.

10 Claims, 3 Drawing Sheets

(56) References Cited

OTHER PUBLICATIONS

Quackenbush J: Microarray data normalization and transformation. *Nat Genet*, 32 Suppl:496-501 (2002).
Yang IV, Chen E, Hasseman JP, Liang W, Frank BC, Wang S, Sharov V, Saeed AI, White J, Li J et al: Within the fold: assessing differential expression measures and reproducibility in microarray assays. *Genome Biol*, 3(11):research0062 (2002).
Saeed AI, Sharov V, White J, Li J, Liang W, Bhagabati N, Braisted J, Klapa M, Currier T, Thiagarajan M et al: TM4: a free, open-source system for microarray data management and analysis. *Biotechniques*, 34(2):374-378 (2003).
Naus S, Richter M, Wildeboer D, Moss M, Schachner M, Bartsch JW: Ectodomain shedding of the neural recognition molecule CHL1 by the metalloprotease-disintegrin ADAM8 promotes neurite outgrowth and suppresses neuronal cell death. *J Biol Chem*, 279(16):16083-16090 (2004).
Buhusi M, Midkiff BR, Gates AM, Richter M, Schachner M, Maness PF: Close homolog of L1 is an enhancer of integrin-mediated cell migration. *J Biol Chem*, 278(27):25024-25031 (2003).
Kanwar JR, Harrison JE, Wang D, Leung E, Mueller W, Wagner N, Krissansen GW: Beta7 integrins contribute to demyelinating disease of the central nervous system. *J Neuroimmunol*, 103(2):146-152 (2000).
Lee JS, Ray R, Chien CB: Cloning and expression of three zebrafish roundabout homologs suggest roles in axon guidance and cell migration. *Dev Dyn*, 221(2):216-230 (2001).
Connor RM, Key B: Expression and role of Roundabout-1 in embryonic *Xenopus* forebrain. *Dev Dyn*, 225(1):22-34 (2002).
Kamholz J, Awatramani R, Menichella D, Jiang H, Xu W, Shy M: Regulation of myelinspecific gene expression. Relevance to CMT1. *Ann N Y Acad Sci*, 883:91-108 (1999).
Manev R, Manev H: 5-Lipoxygenase as a putative link between cardiovascular and psychiatric disorders. *Crit Rev Neurobiol*, 16(1-2):181-186 (2004).
Manev H, Uz T, Sugaya K, Qu T: Putative role of neuronal 5-lipoxygenase in an aging brain. *Faseb J*, 14(10):1464-1469 (2000).
Byrum RS, Goulet JL, Griffiths RJ, Koller BH: Role of the 5-lipoxygenase-activating protein (FLAP) in murine acute inflammatory responses. *J Exp Med*, 185(6):1065-1075 (1997).
Gupta S: A decision between life and death during TNF-alpha-induced signaling. *J Clin Immunol*, 22(4):185-194 (2002).
Wang WJ, Kuo JC, Yao CC, Chen RH: DAP-kinase induces apoptosis by suppressing integrin activity and disrupting matrix survival signals. *J Cell Biol*, 159(1):169-179 (2002).
Vargas DL, Nascimbene C, Krishnan C, Zimmerman AW, Pardo CA: Neuroglial activation and neuroinflammation in the brain of patients with autism. *Ann Neurol*, 57(1):67-81 (2005).
Heneka MT, Schmidlin A, Wiesinger H: Induction of argininosuccinate synthetase in rat brain glial cells after striatal microinjection of immunostimulants. *J Cereb Blood Flow Metab*, 19(8):898-907 (1999).
Akyol O, Zoroglu SS, Armutcu F, Sahin S, Gurel A: Nitric oxide as a physiopathological factor in neuropsychiatric disorders. *In Vivo*, 18(3):377-390 (2004).
Hattori Y, Campbell EB, Gross SS: Argininosuccinate synthetase mRNA and activity are induced by immunostimulants in vascular smooth muscle. Role in the regeneration or arginine for nitric oxide synthesis. *J Biol Chem*, 269(13):9405-9408 (1994).
Lesch KP, Bengel D, Heils A, Sabol SZ, Greenberg BD, Petri S, Benjamin J, Muller CR, Hamer DH, Murphy DL: Association of anxiety-related traits with a polymorphism in the serotonin transporter gene regulatory region. *Science*, 274(5292):1527-1531 (1996).
Bradley SL, Dodelzon K, Sandhu HK, Philibert RA: Relationship of serotonin transporter gene polymorphisms and haplotypes to mRNA transcription. *Am J Med Genet B Neuropsychiatr Genet*, 136(1):58-61 (2005).
Coutinho AM, Oliveira G, Morgadinho T, Fesel C, Macedo TR, Bento C, Marques C, Ataide A, Miguel T, Borges L et al: Variants of the serotonin transporter gene (SLC6A4) significantly contribute to hyperserotonemia in autism. *Mol Psychiatry*, 9(3):264-271 (2004).
Valerie W Hu et al: Gene Expression Profiling of Lymphoblastoid Cell lines From Monozygotyic Twins Discordant in Severity of Autism Reveals Differntial Regulation of Neurologically Relevant Genes. *BMC Genomics*, 7:118 ( 2006).
Lee, Clinical Chemistry, 47:8, 1350-1352, 2001.
Baker, Journal of the National Cancer Institute, vol. 95, No. 7, Apr. 2, 2003, pp. 511-515.
Cheung et al. (2003) Nature Genetics vol. 22, pp. 422-425.
Thisted (1998) What is a P-value? obtained from http://www.stat.uchicago.edu/~thisted 6 pages.
Baron et al. 2006, J Austism Dev Disord 36:973-982.
Nishimura et al. 2007, Human Molecular Genetics, 2007, vol. 16, No. 14, pp. 1682-1698.
Temple University. DNA Microarray Facility website. Copyright 2003, Temple University, 3 pages. obtained from http://replay.waybackmachine.org/20060523221405/http://www.temple.edu/ovpr/ovrpr/sh. Nov. 15, 2010.
Christopher W. Barlett et al., Three autism candidate genes: a synthesis of human genetic analysis with other disciplines, Int. J. Devl Neuroscience 23 (2005) 221-234.
Valerie W. Hu et a., Gene Expression Profiilng Differentiates Autism Case-controls and Phenotypic Variants of Autism Spectrum Disorders: Evidence for Circadian Rhythm Dysfunction in Severe Autism; NIH Public Access, NIH-PA Author Manuscript Austim Res. Apr. 2009, pp. 1-100.
Sek Won Kong et al., Characteristics and Predictive Value of Blood Transcriptome Signature in Males with Autism Spectrum Disorders; PLOS One, Dec. 2012. vol. 7, Issue 12 pp. e49475, pp. 1-13.
Daria Salyakina et al., Copy Number Variants in Extended Autism Spectrum Disorder Families Reveal Candidates Potentially Involved in Autism Risk, PLOS One, Oct. 2011, vol. 6, Issue 10, e26049, p. 1-8.
Susan E. Swanberg et al., Reciprocal co-regulation of EGR2 and MECP2 is disrupted in Rett syndrome and autism, Human Molecular Genetics, 2009, vol. 18, No. 3, pp. 525-534.
International Preliminary Report on Patentability (PCT/IB/326 & PCT/IB/373) dated Feb. 27, 2014 (2 pages).
Written Opinion (PCT/ISA/237) dated Jun. 20, 2012 (7 pages).
International Search Report (PCT/ISA/210) dated Jun. 20, 2012 (4 pages).
"Short Genetic Variations," NCBI Reference SNP (refSNP) Cluster Report: rs2277049, Sep. 2001, 2 pages.
Weiss et al. "A Genome-Wide Linkage and Association Scan Reveals Novel Loci for Autism," NIH Public Access, Oct. 8, 2009, 28 pages, Nature, 461 (7265): 802-808.
David A. Gold et al., "RORα in Genetic Control of Cerebellum Development: 50 Staggering Years", USA, Brain Research, 1140 (2007) pp. 19-25, Elsevier B.V.
Nadia Hadj-Sahraoui et al., Progressive atrophy of cerebellar Purkinje cell dendrites during aging of the heterozygous staggerer mouse (*Rora +/ sg* ), Developmental Brain Research 126, (2001) pp. 201-209, Elsevier Science B.V.
Amber Hogart et al., "15q11-13 GABA$^a$ receptor genes are normally biallelically expressed in brain yet are subject to epigenetic dysregulation in autism-spectrum disorders", USA, Human Molecular Genetics, 2007, vol. 16, No. 6, pp. 691-703, The Oxford Press.
Valerie W. Hu et al., "Novel Clustering of Items From the Autism Diagnostic Interview-Revised to Define Phenotypes Within Autism Spectrum Disorders", The George Washington University Medical Center, Washington, DC, Autism Research, 2, 2009 pp. 67-77.
Timothy R. Hughes et al., "Expression profiling using microarrays fabricated by an ink-jet oligonucleotide synthesizer", 2001 Nature Publishing Group, *Nature Biotechnology*, vol. 19, Apr. 2001 pp. 342-347.
Robert J. Klose et al., "Genomic DNA methylation: the mark and its mediators", Trends in Biochemical Sciences, vol. 31 No. 2 Feb. 2006, pp. 89-97, Elsevier Ltd.
Zhenzhong Li et al., "The Fragile X Mental Retardation Protein Inhibits translation Via Interacting With mRNA", Nucleic Acids Research, 2001, vol. 29, No. 11, pp. 2276-2283, 2001 Oxford University Press.

(56) References Cited

OTHER PUBLICATIONS

Brian C. Froehler et al., "Synthesis of DNA via deoxynucleoside H-phosphonate intermediates", Nucleic Acids Research, vol. 14 No. 13, 1986, pp. 5399-5407, IRL Press Limited, Oxford England.
Vincent Giguere et al., "Isoform-specific amino-terminal domains dictate DNA-binding properties of RORα, a novel family of orphan hormone nuclear receptors", Genes & Development, 1994 by Cold Spring Harbor Laboratory Press, pp. 538-553.
Uwe Masko et al., "Oligonucleotide hybridisations on glass supports: a novel linker for oligonucleotide synthesis and hybridization properties of oligonucleotides synthesised in situ", 1992 Oxford University Press, Nucleic Acids Research, vol. 20, No. 7, pp. 1679-1684.
Mark F. Mehler et al., "Non-coding RNAs in the nervous system", *J Physiol* 575.2 (2006) pp. 333-341.
Raman P. Nagarajan et al., "Reduced MeCP2 Expression is Frequent in Autism Frontal Cortex and Correlates with Aberrant MECP2 Promoter Methylation", Epigenetics, 2006 Landes Bioscience, vol. 1 Issue 4, pp. 172-182.
Michael A. Innis et al., "Optimization of PCRs", PCR Protocols: Aguide to Methods and Applications, 1990, Academic Press, pp. 3-13.
Ann Caviani Pease et al., "Light-generated oligonucleotide arrays for rapid DNA sequence analysis", Proc. Natl. Acad. Sci. USA, Biochemistry, May 1994, vol. 91, pp. 5022-5026.
David J. Lockhart et al., Expression Monitoring by Hybridization to High-Density Oligonucleotide Arrays, Nature Publishing Group, Nature Biotechnology vol. 14, Dec. 1996, 1675-1680.
Dari Shalon et al., "A DNA microarray System for Analyzing Complex DNA Samples Using Two-Color Fluorescent Probe Hybridization", Genome Methods, 1996 by Cold Spring Harbor Laboratory Press, pp. 639-645.
Virgina Goss Tusher et al., "Significance analysis of microarrays applied to the ionizing radiation response", Apr. 24, 2001, PNAS, vol. 98, No. 9 pp. 5116-5121.
Ignatia B. Van Den Veyver et al., Mutations in the gene encoding methyl-CpG-binding protein 2 cause Rett syndrome, Brain & Development, vol. 23, pp. S147-S151, 2001 Elsevier Science B.V.
J. Van Vliet et al., "Epigenetic mechanisms in the context of complex diseases", Cellular and Molecular Life Sciences, Cell. Mol. Life Sci. 64 (2007) pp. 1531-1538.
Margot Moser Richters, Ph.D., et al., "Reactive Attachment Disorder of Infancy or Early Childhood", J. Am. Acad. Child Adolesc. Psychiatry, 33:3. Mar./Apr. 1994, pp. 328-332.
Satoshi Yamashita et al., "Chemical genomic screening for methylation silenced genes in gastric cancer cell lines using 5-aza-2'-deoxycytidine treatment and oligonucleotide microarray", vol. 97, No. 1, pp. 64-71, 2006 Japanese Cancer Association, Cancer Sci.
Tibor Rauch et al., "MIRA-Assisted Microarray Analysis, a New Technology for the Determination of DNA Methylation Patterns, Identifies Frequent Methylation of Homeodomain-Containing Genes in Lung Cancer Cells", *Cancer Res* 2006; 66: pp. 7939-7947, 2006 American Association for Cancer Research.
N. Carolyn Schanen et al., "Epigenetics of autism spectrum disorders", Human Molecular Genetics, 2006, vol. 15, Review Issue No. 2, pp. R138-R150, Oxford University Press.
Philipp Schatz et al., "Rapid analysis of CpG methylation patterns using RNase T1 cleavage and MALDI-TOF", Nucleic Acids Research, vol. 32 No. 21, Oxford University Press 2004; pp. 1-7.
Mark Schena et al., "Parallel human genome analysis: Microarray-based expression monitoring of 1000 genes", Proc. Natl. Acad. Sci. USA, vol. 93, Oct. 1996, Biochemistry, pp. 10614-10619.
International Search Report dated Aug. 26, 2011 (four (4) pages).
Fenghao, Xu et al., "The Role of the LRPPRC (leucine-rich pentatricopeptide repeat cassette) gene in cytochrome oxidase assembly: mutation causes lowered levels of COX (cytochrome c oxidase) I and COX III mRNA", Biochem. J 382 (2004), pp. 331-336.
Traynor, Jeff et al., "Gene expression patterns vary in clonal cell cultures from Rett syndrome females with eight different MECP2 mutations", BMC Medical Genetics, vol. 3, No. 12, Nov. 5, 2002, fifteen pages.
Rapin, Isabelle et al., "Autism: Definition, Neurobiology, Screening, Diagnosis", Pediatric Clinics North America, vol. 55, 2008, pp. 1129-1146.
Ospina, Maria B. et al., "Behavioral and Developmental Interventions for Autism Spectrum Disorder: A Clinical Systematic Review", PLOS One, vol. 3, No. 11, Nov. 2008, e3755, pp. 1-32.
Wang, Bin et al., "Challenges for MicroRNA Microarray Data Analysis", Microarrays, vol. 2, Mar. 25, 2013, pp. 34-50.
Abu-Elneel, Kawther et al., "Heterogeneous dysregulation of microRNAs across the autism spectrum", Neurogenetics, vol. 9, Jun. 19, 2008, pp. 153-161.
Ach, Robert A. et al., "Measuring microRNAs: Comparisons of microarray and quantitative PCR measurements, and of different total RNA prep methods", BMC Biotechnology, vol. 8, No. 69, Sep. 11, 2008, pp. 1-16.
Matson, Johnny L. et al., "Reliability and item content of the Baby and Infant Screen for Children with aUtIsm Traits (BISCUIT): Parts 1-3", Research in Autism Spectrum Disorders, vol. 3, 2009, pp. 336-344, Elsevier.
Newschaffer, Craig J. et al., "Heritable and Nonheritable Risk Factors for Autism Spectrum Disorders", Epidemioligic Reviews, vol. 24, No. 2, 2002, pp. 137-153.
Victor Ambros, "The Functions of Animal MicroRNAs", Insight Review Articles, Nature, vol. 431, Sep. 16, 2004, Nature Publishing, pp. 350-355.
David P. Bartel, "MicroRNAs: Genomics, Biogenesis, Mechanism, and Function", vol. 116, Jan. 23, 2004, Cell Press, pp. 281-297.
A. P. Blanchard et al., "High-Density Oligonucleotide Arrays", Biosensors & Bioelectronics, vol. 11, No. 6/7, 1996, Elsevier Science Ltd., pp. 687-690.
Maria De Fatima Bonaldo et al., "Normalization and Subtraction: Two Approaches to Facilitate Gene Discovery", 1996, Cold Spring Harbor Laboratory Press, vol. 6, pp. 791-806.
Amy A. Caudy et al., "Fragile X-Rated Protein and VIG Associate with the RNA Interference Machinery", Genes & Development, 2002, Cold Spring Harbor Laboratory Press, vol. 16, pp. 2491-2496.
John M. Chirgwin et al., "Isolation of Biologically Active Ribonucleic Acid from Sources Enriched in Ribonuclease", Biochemistry, 1979, American Chemical Society, pp. 5294-5299.
Bryan R. Cullen, "Transcription and Processing of Human MicroRNA Precursors", Molecular Cell, vol. 16, Dec. 22, 2004, pp. 861-865.
Joseph Derisi et al., "Use of a cDNA Microarray to Analyse Gene Expression Patterns in Human Cancer", nature genetics vol. 14, 1996, Nature Publising Group, pp. 457-460.
Antonio J. Giraldez et al., "MicroRNAs Regulate Brain Morphogenesis in Zebrafish", vol. 308, www.sciencemag.org, 2005, (seven (7) pages).
Abha R. Gupta et al., "Recent Advances in the Genetics of Autism", Biol Psychiatry, vol. 61, www.sobp.org/jorunal, 2007, pp. 429-437.
Mark Schena et al., "Quantitative Monitoring of Gene Expression Patterns with a Complementary DNA Microarray", ProQuest, Science, vol. 270, 1995, pp. 467-470.
Akira Ishizuka et al., "A *Drosophila* Fragile X Protein Interacts with Components of RNAi and Ribosomal Proteins", Genes & Development, vol. 16, 2002, CSH Press, pp. 2497-2508.
Peng Jin et al., "RNA MicroRNAs in Fragile X Mental Retardation", Nature Cell Biology, vol. 6, No. 11, Nov. 2004, Nature Publising Group, pp. 1048-1053.
V. Narry Kim, "MicroRNA Biogenesis: Coordinated Cropping and Dicing", www.nature.com/review/molecellbio, vol. 6, May 2005, pp. 376-385.
Rebecca Muhle et al., "The Genetics of Autism", Pediatrics, American Academy of Pediatrics, vol. 113, No. 5, May 2004, (Seventeen (17) pages).
Joseph Piven, MD., et al., Broader Autism Phenotype: Evidence from a Family History Study of Multiple-Incidence Autism Families, Am J. Psychiatry, vol. 154, No. 2, Feb. 1997, pp. 185-190.
Franck Polleux et al., Toward a Developmental Neurobiology of Autism, Menal Retardation and Development Disabilities Research Reviews, vol. 10, 2004, Wiley-Liss, Inc., pp. 303-317.

(56) References Cited

OTHER PUBLICATIONS

Susan L. Santangelo et al., "What is Known about Autism", Genomics in Health and Disease, Am J. Pharmacogenomics, vol. 5, No. 2, 2005, pp. 71-92.
Amanda L. Yonan et al., "A Genomewide Screen of 345 Families for Autism-Susceptibility Loci", Am. J. Hum. Genet., vol. 73, 2003, pp. 886-897.
Fred R. Volkmar, MD., et al., "Field Trial for Autistic Disorder in DSM-IV", Am J. Psychiatry, vol. 151, No. 9, Sep. 1994, pp. 1361-1367.
International Search Report dated Mar. 14, 2011.
Burmistrova, O.A. et al., "MicroRNA in Schizophrenia: Genetic and Expression Analysis of miR-130b (22q11)", Biochemistry, 2007, vol. 72, No. 5, pp. 578-582, Pleiades Publishing, Ltd.
Heinzen, Erin L. et al., "Tissue-Specific Genetic Control of Splicing: Implications for the Study of Complex Traits", PLOS Biology, vol. 6, No. 12, Dec. 2008, pp. 2869-2879.
Howlin, Patricia, "Autism Spectrum Disorders", Psychiatry, vol. 5, Issue 9, Sep. 2006, pp. 320-324, Elsevier, Ltd.
International Search Report dated Sep. 17, 2010 (two (2) sheets).
James et al., "Metabolic biomarkers of increased oxidative stress and impaired methylation capacity in children with austim", The American Journal of Clinical Nutrition, 2004, vol. 80, pp. 1611-1617 (seven (7) sheets).
Marshall et al., "Structural Variation of Chromosomes in Autism Spectrum Disorder", The American Journal of Human Genetics, Feb. 2008, vol. 82, pp. 477-488 (twelve (12) sheets).
Ming et al., "Increased excretion of a lipid peroxidation biomarker in autism", Prostaglandins, Leukotrienes and Essential Fatty Acids, 2005, vol. 73, pp. 379-384 (six (6) sheets).
Search results for query: slc6a4 from http://www.affymetrix.com/analysis/netaffx/showresults.affx accessed [Aug. 15, 2012].
Search results for query: robo1 from http://www.affymetrix.com/analysis/netaffx/showresults.affx accessed [Aug. 15, 2012].
Search results for query: alox5ap from http://www.affymetrix.com/analysis/netaffx/showresults.affx accessed [Aug. 15, 2012].
Search results for query: ass from http://www.affymetrix.com/analysis/netaffx/showresults.affx accessed [Aug. 15, 2012].
Search results for query: chl1 from http://www.affymetrix.com/analysis/netaffx/showresults.affx accessed [Aug. 15, 2012].
Search results for query: dapk1 from http://www.affymetrix.com/analysis/netaffx/showresults.affx accessed [Aug. 15, 2012].
Search results for query: egr2 from http://www.affymetrix.com/analysis/netaffx/showresults.affx accessed [Aug. 15, 2012].
Search results for query: il6st from http://www.affymetrix.com/analysis/netaffx/showresults.affx accessed [Aug. 15, 2012].

* cited by examiner

FIG. 3

Principal components analysis of microarray data from the 5 sets of monozygotic twins with ASD, with each color representing a separate pair of twins. Each point on the graph represents a dye-reversal experiment on a given twin pair. This data suggests that the principal factor affecting overall gene expression profile is genotype. Note that even the 2 pairs of twins who share the same mother (           ) are distinguishable from each other.

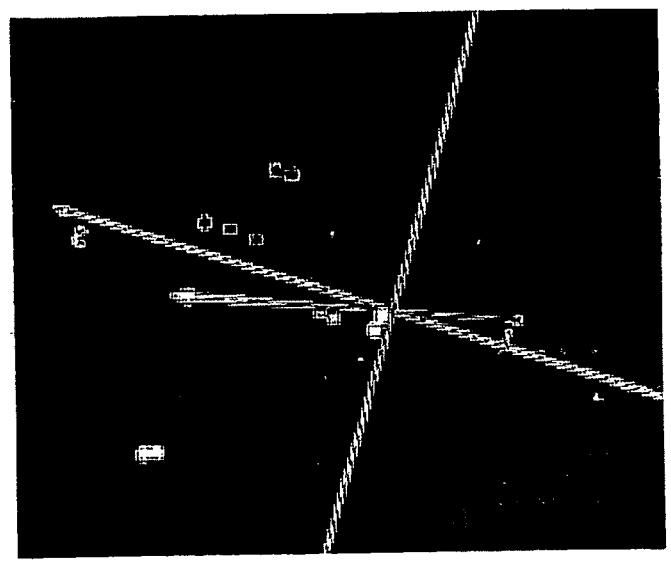

METHOD AND KIT FOR DIAGNOSING AUTISM USING GENE EXPRESSION PROFILING

PRIORITY

This application claims the benefit under 119(e) of U.S. 60/789,593 filed 6 Apr. 2007.

BACKGROUND

1. Field of the Invention

This invention relates to DNA microarray technology, and more specifically to methods and kits for identifying autism and autism spectrum disorders in humans.

2. Description of the Prior Art

Several publications are referenced in this application in parentheses in order to more fully describe the state of the art to which this invention pertains. Full citations for these references are found at the end of the specification. The disclosure of each of these publications is incorporated by reference herein in their entirety.

The autism spectrum encompasses a set of complex multigenic developmental disorders that severely impact the development of language, non-verbal communication, and social skills, and are associated with odd, stereotyped, repetitive behavior and restricted interests. To date, diagnosis of these neurologically based disorders relies predominantly upon behavioral observations often prompted by delayed speech or aberrant behavior, and there are no known genes that can serve as definitive biomarkers for the disorders.

Autism and related autism spectrum disorders (including Asperger's Syndrome and pervasive developmental disorder-not otherwise specified (PDD-NOS)) are considered to be among the most devastating psychiatric illnesses affecting children. The three core symptoms of autism spectrum disorders (ASD) are: 1) deficits in social interactions and understanding, 2) aberrant communication and/or language development, and 3) restricted, repetitive, and stereotyped behaviors [1]. To date, there are no definitive molecular or genetic markers that allow unequivocal diagnosis of ASD, with the exceptions of tuberous sclerosis, Rett's Syndrome, and Fragile X Syndrome [2-12]. Together, these genetically defined mutations are present in only a minority of individuals (<10%) within the broad autism spectrum. The majority of diagnoses are dependent on behavioral characteristics, according to DSM-IV guidelines, using questionnaires such as the Autism Diagnostic Interview-Revised (ADI-R) [13] or the Autism Diagnostic Observation Schedule (ADOS) [14], which are structured to evaluate children who are approximately 2 or older in mental age. Although the guidelines are relatively clear, the individual rater's (eg., parents, teachers, clinicians, therapists) perception of the evaluated behavior leaves much room for ambiguity. Moreover, with the more mildly affected individuals (eg., with Asperger's Syndrome), diagnosis is often not made until well after the child starts school and, even then, the child is often diagnosed with other more common disorders (such as attention deficit disorder or learning disability) before Asperger's Syndrome is considered, which delays appropriate intervention and effective educational programming. Thus, there is a great need to identify biomarkers that can be used consistently in a clinical setting to diagnose ASD. Furthermore, it is important to identify biological processes that are associated with specific ASD phenotypes in order to design effective drug therapies targeted to specific individuals.

Although genetic linkage analyses have identified numerous candidate genes for autism [15], there is little consistent data that would support the use of any (or a combination) of these as biomarkers for ASD. Furthermore, each candidate gene alone lends little insight into the pathophysiology of these disorders, which are believed to arise from dysregulation of multiple genes. Recently, attention has turned to transcriptional profiling approaches [16-19], which involve simultaneous, large-scale expression analysis of thousands of genes on a cDNA (or oligonucleotide) microarray slide, to unravel complex psychiatric disorders. The advantage of transcriptional profiling using microarrays is the ability to study multiple genes in the context of functional gene networks within a living cell, as opposed to forward genetic approaches. So far, application of microarrays to the study of autism has been described in just one study on post-mortem brain tissue from autistic subjects and matched tissue controls [20]. Thirty genes were identified as being differentially expressed in autistic brain samples relative to matched tissue controls on a combination of 2 separate array platforms containing 588 or 9374 cDNA probes, indicating that autism is associated with multiple disturbances in gene expression. Of this list, only a few genes related specifically to neurological functions and, of these, the glutamate receptor system was targeted for further study. In a similar vein, a recent bioinformatics analysis of autism positional candidate genes using biological databases and computational gene network prediction software demonstrates that the often disparate results from genetic studies implicating a multitude of different genes can be coalesced into interconnected but distinct pathways centered on a specific gene or genes (e.g., FOS and TP53), or on a particular biological theme, e.g., apoptosis [15]. Both of these studies suggest the involvement of multiple genes not previously associated with autism and illustrate the power of using a global approach to study this complex disorder.

The experimental strategy used in the study reported here was designed to tease out differences in gene expression among genetically identical individuals with ASD which might relate to observed differences in the degree of expression of autistic symptoms. Inasmuch as natural variations in gene expression are especially low for monozygotic twins [21, 22], such a strategy has been shown to be useful in identifying candidate genes for bipolar disorder [23] and osteoporosis [24]. Moreover, lymphoblastoid cell lines (LCL) derived from blood cells of autistic individuals were used in this study to explore the possibility that biomarkers for autism could be expressed in easily accessible peripheral cells. Indeed, it has been reported previously that LCL from individuals with bipolar disorder displayed altered gene expression in both postmortem brain tissue and lymphoblasts, although one of the genes, LIM, was altered in the opposite direction in LCL [25]. Follow-up genetic association analyses of this gene demonstrated association of a single nucleotide polymorphism with bipolar disorder [26], indicating the usefulness of LCL and DNA microarray analyses in identifying potential biomarkers of a complex neurological disease.

While studies of gene expression in brain tissue may lead to a better understanding of the mechanistic basis for ASD, it is not an appropriate target for diagnostic assays. Ideally, diagnostic assays should use easily obtained patient samples such as blood, although there is no evidence that gene expression or other markers exist in the peripheral blood of ASD patients. However, one may hypothesize that ASD might arise, in part, through dysregulation of expression of specific neuronal genes and that expression differences between affected and unaffected individuals might be present in tissues other than brain. As a test of this hypothesis, we chose to use DNA microarray analysis to examine gene expression in LCL derived from peripheral blood lymphocytes.

SUMMARY

Here we report the first study using a genome-scale approach to identify biomarkers for autism. We demonstrate by gene expression profiling on DNA microarrays that: 1) LCL derived from five monozygotic twin pairs discordant for diagnosed autism and/or language impairment show differential gene expression; 2) a number of the most differentially expressed genes are present in pathways critical to the development and function of the nervous system; 3) there appears to be a quantitative relationship between the severity of the autistic phenotype exhibited by the twins and the expression level of certain genes relative to that of the respective genes in cell lines from non-affected siblings; and 4) approximately half of the most highly differentially expressed genes map in silico to previously reported chromosomal regions containing autism susceptibility genes or quantitative trait loci.

Specifically, one embodiment of the present inventive subject matter includes a method of screening for an Autism Spectrum Disorder in a patient by analyzing differential gene expression patterns by DNA microarray analysis, comprising the steps of: obtaining a nucleic acid sample from peripheral cells of a patient; performing DNA microarray analysis on said nucleic acid samples to obtain a gene expression analysis data set; and comparing said data set to a control data set corresponding to a gene ensemble of differentially expressed genes indicative of Autism Spectrum Disorder, wherein Autism Spectrum Disorder is indicated upon observing statistically significant differential gene expression in 20 or more genes.

In preferred embodiments, the gene ensemble is a gene ensemble according to Table 1, a gene ensemble according to Table 3, a gene ensemble according to Table 4, or a gene ensemble according to Table 5.

Preferred embodiments also include gene ensembles comprising a combination of genes listed in Tables herein, but specifically Tables 1, 3, 4, and 5.

In a preferred embodiment, the peripheral cells comprise lymphoblastoid (lymphoblasts) cells, and more preferably white blood cells. In another preferred embodiment, the peripheral cells are mucosal epithelial cells from buccal swabs, particularly advantageous when considering a neonatal or pediatric patient population.

The control expression profile is preferably of nonautistic individuals, but may also be reflective of autistic individuals depending on how the method is performed.

The DNA microarray analysis preferably includes screening methods selected from the group consisting of large scale microarray analysis, qPCR analysis, Western analysis, and focused gene chip analysis. However, other equivalent techniques known to persons of skill in the art are also contemplated as included herein.

The gene ensemble of differentially expressed genes indicative of Autism Spectrum Disorder preferably include genes involved in inflammation, and more preferably neuroinflammation.

Autism spectrum disorders herein include autism, Asperger's Syndrome, and pervasive developmental disorder-not otherwise specified (PDD-NOS).

The present inventive subject matter also includes an assay for screening drugs and other agents for ability to treat autism spectrum disorder or a disease or disorder related thereto, said assay comprising the steps of: culturing an observable cellular test colony which produces a differential gene expression profile representative of an autism spectrum disorder and which has been inoculated with the drug or agent to be assayed; harvesting a cellular extract from the cellular test colony; determining the level of gene expression in the test colony; and comparing the level of gene expression in the test colony to a control level of gene expression which represents a test colony not inoculated with the drug, or to the test colony prior to inoculation with the drug or agent, wherein the ability of the drug or agent to modulate the production, stability, degradation or activity of gene expression is indicative of the drug or agent's ability to treat autism spectrum disorder.

In a preferred embodiment the Autism Spectrum Disorder is indicated upon observing statistically significant differential gene expression in 20 or more genes. In preferred assay embodiments, the differential gene expression profile representative of an autism spectrum disorder is characterized by a gene ensemble selected from gene ensembles according to. Table 1, Table 3, Table 4, or Table 5. Preferred embodiments also include gene ensembles comprising a combination of genes listed in Tables herein, but specifically Tables 1, 3, 4, and 5.

Also contemplated herein are test kits to facilitate diagnosis and treatment of autism spectrum disorders, comprising: an indicator of expressed genes representative of a patient that has a differential gene expression pattern indicative of Autism Spectrum Disorder; reagents and equipment for analyzing a sample of epithelial cells and obtaining a differential gene expression pattern; and directions for use of said kit. Such kits are generally well known in the art, with the novel features herein stemming from the differential gene expression indicative of ASD. In preferred embodiments, the sample comprises white blood cells and also mucosal epithelial cells from a buccal swab, i.e. a cheek swab. It is contemplated that the kit reagents and equipment comprise cDNA microarray analysis materials.

Further preferred embodiments herein include a computer-implemented method for analyzing gene expression to screen for an autism spectrum disorder is provided wherein the method comprises the steps of: compiling data comprising a plurality of measured gene expression signals derived from cDNA microarray analysis of lymphoblastoid cells into a form suitable for computer-based analysis; and analyzing the compiled data, wherein the analyzing comprises identifying gene networks from a number of uprelated biomarker genes and downregulated biomarker genes, wherein the biomarker genes are genes that have a reported role in inflammation. In a preferred embodiment, the genes are ASS, ALOX5AP (FLAP), DAPK1, AND IL6ST, as listed in bold in Table 1. It is also contemplated that the biomarker genes are genes involved in nervous system development and function. These include ALOX5AP (FLAP), CD44, CHL1, EGR2, F13A1, FLT1, IL6ST, ITGB7, and NAGLU.

Along these lines, the inventive contribution also includes a computer-readable medium on which is encoded programming code for analyzing autism spectrum disorder gene expression from a plurality of data points which comprises a gene ensemble which is filtered using a log 2 cutoff of 0.58.

TABLE 1 is a chart showing significant up- and down-regulated genes from SAM analysis of microarray experiments on 3 sets of monozygotic twins discordant for autism diagnosis.

TABLE 2 is a chart showing expression of ASS, CHL1, AND FLAP.

TABLE 3 is a chart showing network focus genes from Ingenuity Pathways Analysis.

TABLE 4 shows the relative expression of candidate genes in monozygotic concordant twin pairs with differential language impairment and in norm twins.

TABLE 5 shows significant genes across give sets of twins with ASD.

TABLE 6 is a global functional analysis.

TABLE 7 shows differentially expressed candidate genes from microarray experiments mapped into a silico to autism susceptibility genes.

SUPPLEMENTARY TABLE 2 is a table showing case description of subjects from whom LCL were derived and used in the study.

SUPPLEMENTAL TABLE 3 shows primers used for qualitative RT-PCR analyses.

BRIEF DESCRIPTION OF THE FIGURES

FIG. 3 shows a principal components analysis of microarray data from 5 sets of monozygotic twins with ASD.

DETAILED DESCRIPTION OF THE PREFERRED EMBODIMENTS

List of Abbreviations

Figure 1:
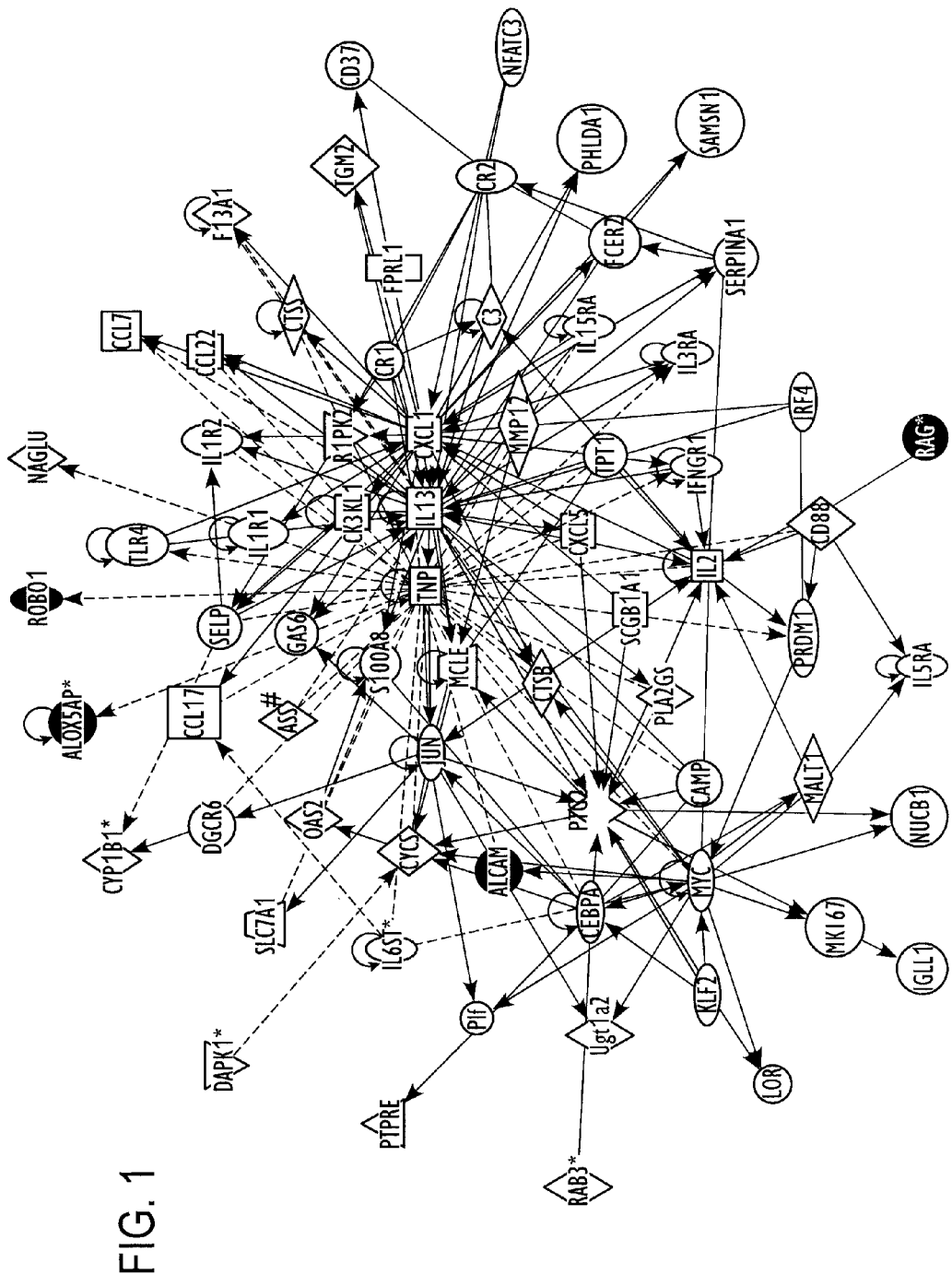
FIG. 1 Gene networks showing inter-relationship between differentially expressed genes in LCL from 3 discordant autistic twin sets using Ingenuity Pathways Analysis software. The over-expressed (red) and under-expressed (green) genes were identified as significant using SAM analysis (FRD=26.4%) of microarray data across 3 twin pairs. The log 2 expression ratio cutoff was set at ±0.58 and was based upon the mean values for each gene. Genes within this network that have a reported role in nervous system development and function include: ASS, ALOX5AP (FLAP), DAPK1, F13A1, IL6ST, NAGLU, PTGS2, and ROBO1. Gray genes are present but do not meet expression cutoff.

ADIR: Autism Diagnostic Interview-Revised
ADOS: Autism Diagnostic Observation Schedule AGRE: Autism Genetic Resource Exchange
ASD: autism spectrum disorders
ASS: argininosuccinate synthetase
CHL1: cell adhesion molecule with homology to L1CAM
DAPK1: death-associated protein kinase 1
EGR2: early growth response 2 protein (Krox-20)
FLAP: 5-lipoxygenase activating protein
5-HTT: 5-hydroxytryptamine (serotonin) transporter
ITGB7: integrin beta-7LCL: lymphoblastoid cell lines
PPVT: Peabody Picture Vocabulary Test
ROBO1: roundabout, axon guidance receptor The following definitions are provided to facilitate an understanding of the present invention:

With reference to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. An "isolated nucleic acid molecule" may also comprise a cDNA molecule or a recombinant nucleic acid molecule.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The term "oligonucleotide," as used herein refers to sequences and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art. For instance, one common formula for calculating the stringency conditions required to achieve hybridization between nucleic acid molecules of a specified sequence homology is set forth below (Sambrook et al., 1989):

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The term "probe" as used herein refers to an oligonucleotide, polynucleotide or DNA molecule, whether occurring naturally as in a purified restriction enzyme digest or produced synthetically, which is capable of annealing with or specifically hybridizing to a nucleic acid with sequences complementary to the probe. The probes of the present invention refer specifically to the oligonucleotides attached to a solid support in the DNA microarray apparatus such as the glass slide. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "specific binding pair" as used herein includes antigen-antibody, receptor-hormone, receptor-ligand, agonist-antagonist, lectin-carbohydrate, nucleic acid (RNA or DNA) hybridizing sequences, Fc receptor or mouse IgG-protein A, avidin-biotin, streptavidin-biotin, amine-reactive agent-amine conjugated molecule and thiol-gold interactions. Various other determinant-specific binding substance combinations are contemplated for use in practicing the methods of this invention, such as will be apparent to those skilled in the art.

The term "detectably label" is used herein to refer to any substance whose detection or measurement, either directly or indirectly, by physical or chemical means, is indicative of the presence of the target bioentity in the test sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

Polymerase chain reaction (PCR) has been described in U.S. Pat. Nos. 4,683,195, 4,800,195, and 4,965,188, the entire disclosures of which are incorporated by reference herein.

The phrase "obligate carrier" refers to an individual who is a heterozygous carrier of a gene associated with an autosomal recessive disorder.

A DNA microarray (also commonly known as gene chip, DNA chip, or biochip) is a collection of microscopic DNA spots attached to a solid surface, such as glass, plastic or silicon chip forming an array. Exemplary cDNA microarrays of the invention are commercially available and may be purchased from such companies as Agilent Technologies, Affymetrix Inc. (Santa Clara, Calif.), Nanogen (San Diego, Calif.) and Protogen Laboratories (Palo Alto, Calif.).

Microarrays are used to quantify mRNAs transcribed from different protein-encoding genes. RNA is extracted from a cell or tissue sample, then converted to cDNA. Fluorescent tags, (usually Cy3 and Cy5) are enzymatically incorporated into the newly synthesized cDNA or can be chemically attached to the new strands of DNA. A cDNA molecule that contains a sequence complementary to one of the single-stranded probe sequences on the array will hybridize, via base pairing, to the spot at which the complementary reporters are affixed. The spot will then fluoresce (or glow) when examined using a microarray scanner. The fluorescence intensity of each spot is then evaluated in terms of the number of copies of a particular mRNA, which ideally indicates the level of expression of a particular gene.

DNA microarrays can be used to detect RNAs that may or may not be translated into active proteins. This analysis is termed "expression analysis" or expression profiling. Since there can be tens of thousands of distinct reporters on an array, each microarray experiment can accomplish the equivalent number of genetic tests in parallel.

In a preferred embodiment of the invention, cDNA microarrays were prepared on aminoalkylsilane coated microscope, slides (Sigma, St Louis, Mo.) using a pin-and-ring arrayer (Affymetrix 417, Bedford, Mass.).

Oligonucleotide microarrays (or single-channel microarrays), are also contemplated herein. There, the probes are designed to match parts of the sequence of known or predicted mRNAs. There are commercially available designs that cover complete genomes from companies such as Affymetrix, or Agilent. These microarrays give estimations of the absolute value of gene expression and therefore the comparison of two conditions requires the use of two separate microarrays.

Long Oligonucleotide Arrays are composed of 60-mers, and are produced by either ink-jet or robotic printing. Short Oligonucleotide Arrays are composed of 25-mer oligos, and are produced by photolithographic synthesis (Affymetrix). More recently, Maskless Array Synthesis from NimbleGen Systems has combined flexibility with large numbers of probes. Arrays can contain up to 390,000 spots, from a custom array design.

Statistical analysis of the expression differential can be performed using the 1-sample t-test, but also may include other statistical methods. For example, the one-class Significance Analysis of Microarrays (SAM) analysis is contemplated as within the scope of the inventive subject matter.

The following examples provide illustrative methods of practicing the instant invention, and are not intended to limit the scope of the invention in any way.

EXAMPLES

Differential gene expression in lymphoblastoid cell lines from monozygotic twins discordant for classic autism To determine whether LCL derived from individuals with autism exhibit patterns of gene expression that may be relevant to autism spectrum disorders (ASD), gene expression profiling was performed on LCL derived from 3 sets of male monozygotic twins, one of each pair who met standard diagnostic criteria for autism based on the ADI-R. In each case, the other twin, while not clinically autistic, exhibited autistic traits and was classified either as "broad spectrum" or "not quite autistic" according to guidelines described by the Autism Genetic Resource Exchange (AGRE) repository (http://www.agre.org). Two of the three twin pairs had an unaffected sibling and these were also used for comparison with their respective twin siblings. All of these assays employed an experimental design in which RNA from twin siblings were cohybridized on two-color spotted microarrays containing 39,936 human cDNA elements. Each microarray experiment involved dye-reversal replicates, and was performed in duplicate or, in one case, triplicate for the different sets of twins. The mean log 2 ratios of each gene were used for SAM analyses of the biological replicates.

Principal components analysis (PCA) of the combined microarray data with respect to samples from the 3 discordant twin sets showed that genotype is responsible for the major portion of the variation in differential gene expression, reflecting the expected transcriptome heterogeneity among unrelated individuals (Supplementary FIG. 1). The microarray data from the 3 sets of discordant twins was analyzed using SAM in order to identify genes that were significantly different from log 2=0 across the biological replicates (n=3). Twelve hundred genes were identified as significant with a median FDR of 26%. Twenty-five genes were found to be up-regulated at least 1.5-fold in the more severely affected twin relative to the other twin (log 2(ratio)≥0.58) and 19 genes were down-regulated by at least 1.5-fold (Table 1). Of these, nine of the 26 known genes (representing seven unique genes) correspond to genes involved in neurological development, function, or disease. Because of this surprising finding, we used quantitative RT-PCR (qPCR) to confirm the differential expression of these specific genes. As shown in Table 1, qPCR confirmed the relative expression levels of all but one of these, including argininosuccinate synthetase (ASS), close homologue of L1 (CHL1), cell death-associated kinase (DAPK1), 5-lipoxygenase-activating protein (ALOX5AP or FLAP), interleukin-6 signal transducer (IL6ST), and Roundabout homolog 1 precursor (ROBO-1).

Moreover, when the expression profile of cells from the autistic twin was directly compared against that of his respective normal sibling in a dye-reversal microarray experiment, neurologically relevant genes represented 3 of the top 5 most differentially expressed genes (Table 2). Interestingly, the mean log 2(ratio) of each of these, ASS, CHL1, and FLAP, are higher for the autistic twin than for the more mildly affected twin when each is compared against their respective normal sibling, suggesting a quantitative relationship between differential gene expression (relative to normal individuals) and severity of autistic symptoms. These quantitative differences have also been confirmed by qPCR analyses.

Network analysis shows overlap of pathways involving differentially expressed, neurologically relevant genes Pathway analysis using Ingenuity Pathways Analysis Software of the significant genes from the SAM analysis further revealed that 25 out of 58 network focus genes with log 2(ratio) greater than ±0.58 (±1.5-fold) in at least one discordant twin set are involved in neurological function or disease (Table 3). This expression cutoff was selected because of reports in the literature that 1.47-fold increases or decreases in gene expression are generally reproducible when Lowess normalization is used (Yang et al, 2002), and our own ability to confirm expression changes of at least 1.5-fold by qPCR. Of particular note is the gene network that is derived from pathway analysis of the mean expression values (with log 2 ratio ≥±0.58) across 3 sets of discordant twins which shows that the majority of significantly differentially expressed genes are part of an extended network centered on TNF (FIG. 1). The neurological functions of 7 of these network focus genes are described in Table 3. The collective data from the above-mentioned microarray and qPCR studies suggested a short list of novel candidate autism susceptibility genes for further evaluation.

Differential expression of autism candidate genes in "concordant" autistic twins Expression analysis of autism candidate genes in LCL from two sets of twins in which both individuals were diagnosed as autistic surprisingly showed differential expression of several of the candidate genes (Table 4). However, in each case, the "concordant" autistic twin siblings were found to be discordant with respect to severity of language impairment based on each twin's scores on the Peabody Picture Vocabulary Test (PPVT) (see Supplementary Table X for profile of subjects studied). Thus, when microarray data from the more language-impaired twin (lower percentile PPVT score) was compared relative to the less impaired twin, the differential gene expression profile was consistent with the results obtained from the "discordant" twin sets. This result underscores the importance of considering autistic phenotype and/or severity as a means of reducing heterogeneity of gene expression in the search for biomarkers of autism. Interestingly, as shown in Table 4, expression analysis of the candidate genes in cells from monozygotic nonautistic twins demonstrated that two of the genes, CHL1 and ROBO1, were differentially expressed. However, it is worth noting that this set of "normal" twins has two autistic siblings. It is therefore possible that the differential expression of these two neurologically relevant genes is not coincidental, but does not, by itself, meet the threshold for association with an autistic phenotype. Alternatively, this result might suggest that these genes are not involved in autism. Clearly, this observation on only one set of normal twins warrants further investigation preferably with twins with no autism in their family background, but it is difficult to obtain normal monozygotic twins with no autistic siblings from the AGRE repository which focuses on collecting samples from pedigrees with familial autism.

The serotonin transporter (5-HTT) gene is also differentially expressed in lymphoblastoid cells from monozygotic twins discordant in severity of autism and/or language impairment To evaluate whether differential expression of the serotonin transporter (5-HTT), which is strongly implicated in autism, can be detected in LCL from the autistic and nonautistic twins, qPCR analyses were performed, as 5-HTT is not represented on the microarray platform. Results indicated that, while there is no difference in 5-HTT expression between the nonautistic twins, there is a significant decrease in expression in the more severely affected twin in all of the autistic twin pairs studied, as shown in Table 4. Reduced expression of 5-HTT in blood-derived cells may explain hyperserotonemia in a subset of autistic individuals [27]. It should also be noted that a polymorphism in the promoter region of 5-HTT which results in reduced transcription of 5-HTT is a factor in anxiety related traits [28, 29], common in autism. The present finding suggests that LCL, or their precursor blood lymphocytes, may be useful as reporter cells to evaluate neurologically relevant gene expression differences between autistic and normal individuals.

Figure 2:
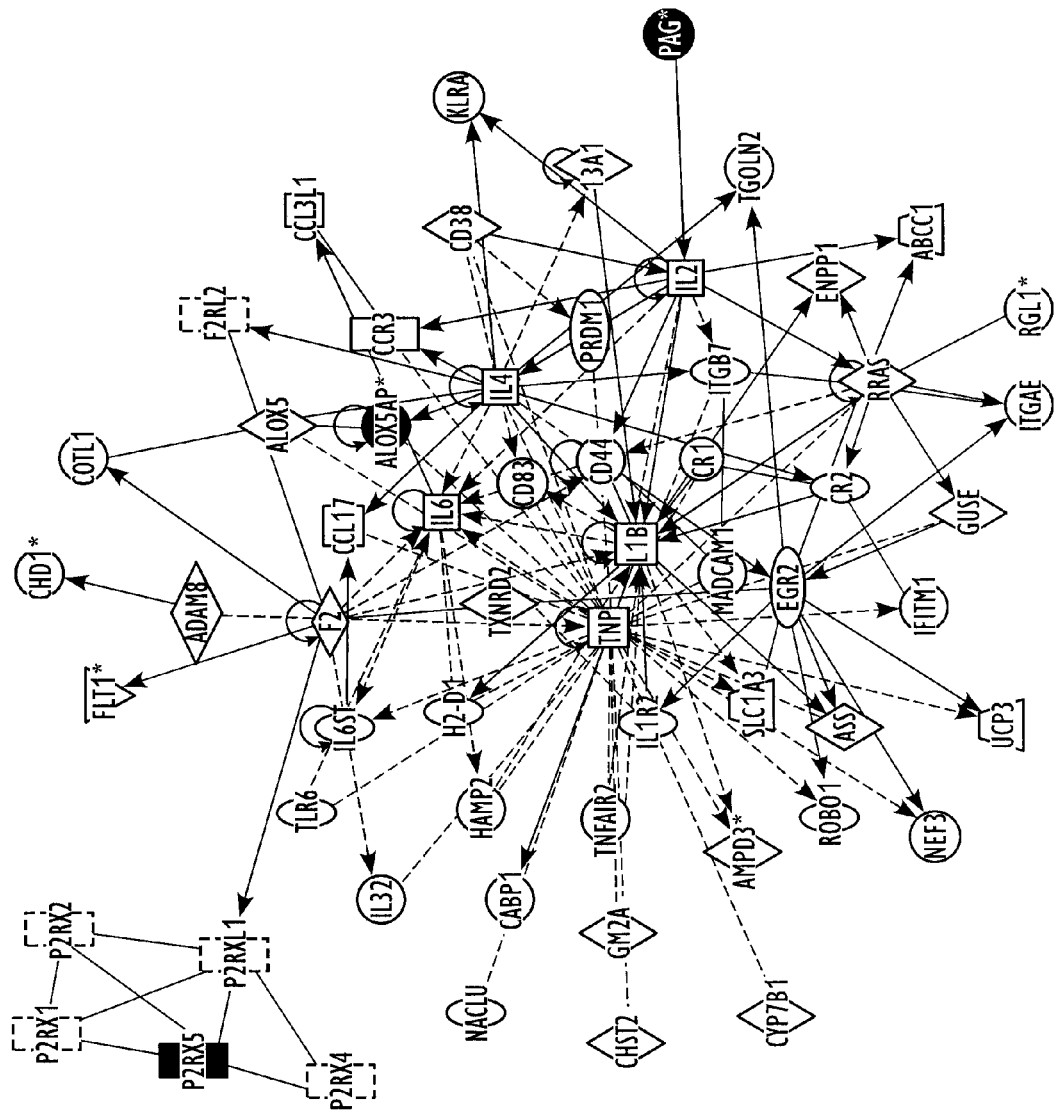
FIG. 2 Gene networks showing inter-relationship between differentially expressed genes in lymphoblastoid cells lines from monozygotic twins discordant in severity of autism spectrum disorder and/or language impairment. The over-expressed (red) and under-expressed (green) genes were identified as significant using SAM analysis (FDR=15.6%) of microarray data across 5 twin pairs. The log 2 expression ratio cutoff was set at ±0.58 and was based upon the mean values for each gene. Differentially expressed genes within this network that have a reported role in nervous system development and function include: ALOX5AP (FLAP), CD44, CHL1, EGR2, F13A1, FLT1, IL6ST, ITGB7, and NAGLU. Gray genes are present but do not meet expression cutoff.

Network and global functional analyses of the pooled microarray data on monozygotic twins with autism highlight genes involved in nervous system development and function Because of the observed relationship between severity of symptoms and differential expression of candidate genes across the 5 autistic twin pairs studied, SAM was applied to microarray data from all 5 sets of twins to identify genes that were significantly up- or down-regulated across all twin pairs, each pair of which exhibited differential severity with respect to language ability (Table 5). Once again, pathway analysis of the differentially expressed significant genes revealed an extended network centered on TNF, connecting a number of neurologically relevant genes (FIG. 2). Global functional analysis of the significant differentially expressed genes from 5 pairs of twins further shows that genes related to "nervous system development and function" are among the most statistically significant, enriched genes across the 5 sets of twins (Table 6).

In silico mapping of differentially expressed genes to chromosomal regions containing autism candidate genes or quantitative trait loci (QTLs)

Although most of the differentially expressed genes identified in this study are novel candidate genes with respect to autism, Table 7 shows that 6 out of 8 of the novel candidate genes listed in Table 4 [and approximately half of the differentially expressed genes listed in Tables 3 and 5 (Supplementary Table 1)] map to chromosomal regions containing previously reported autism candidate genes or recently identified QTLs for spoken language and nonverbal communication. This observation is interesting in that the overlay of expression data onto genetic data allows us to focus on expressed, neurologically relevant genes that may relate to the functional phenotype. Taken together with the network and global functional analyses described above, these results present a compelling argument for further investigation of blood-derived cells as surrogates to identify biomarkers for autism.

DISCUSSION

These studies show, for the first time, that candidate genes for autism may be expressed in peripheral cell lines derived from individuals with ASD. This observation is a critical step towards development of a diagnostic screen for autism based on biomarker detection in an easily accessible tissue (i.e., blood)

In this study, DNA microarrays containing ~40K human cDNA probes were utilized to examine differences in gene expression profiles in LCL derived from 5 pairs of monozygotic twins with ASD. Three sets of twins were discordant with respect to clinical diagnosis of autism, and 2 sets (both diagnosed as autistic) differed with respect to severity of language impairment. The most remarkable finding of this study is that global functional analysis of the significant differentially expressed genes in LCL from these 5 sets of twins identifies "Nervous system development and function" as a top "high level function" that is significantly enriched within the gene datasets (Table 6). Moreover, in silico mapping of our gene expression data demonstrates that many of the differentially expressed genes are located in or close to chromosomal regions previously identified as autism susceptibility loci by genetic analyses (Table 7 and Supplementary Table 3). Quantitative RTPCR analysis has further confirmed the differential expression of a subset of our novel candidate genes in the majority of twin sets studied. Several of these candidate genes and their associated gene networks may provide insight into potential mechanisms involved in the autistic phenotype(s). One of the striking results of the pathway analyses is that a relatively large number of the differentially expressed, neurologically relevant genes are linked in networks that are centered on genes involved in inflammation (see FIGS. 1 and 2): These include the proteins ASS, ALOX5AP (FLAP), DAPK1, F13A1, IL6ST, NAGLU, and ROBO1. The protein ASS regulates the rate-limiting step involved in nitric oxide (NO) production through regeneration of arginine from citrulline, a byproduct of the nitric oxide synthetase (NOS) reaction [30]. Since NO is a major signaling molecule in the brain that has been implicated in several psychiatric disorders, including autism [31], the increased expression of ASS may be of potential relevance to the autistic phenotype. ASS has also been shown to be induced in a rat model of brain inflammation [32], which would be consistent with the hypothesis that neural inflammation may play a role in autism [33]. DAPK1, a cell death-associated serine/threonine kinase which is involved in suppression of integrin activity and disruption of matrix survival signals [34], is also induced by inflammation [35]. Furthermore, the fact that IL6ST (gp130) is increased in LCL from the more severely affected twin, may complement previous observations that IL-6 is the most elevated inflammatory cytokine in the middle frontal gyms and anterior cingulate gyms of brain autopsy tissue from autistic individuals [33]. While upregulation of ASS, DAPK1, and IL6ST may be responses to inflammation, ALOX5AP (FLAP) mediates inflammation through activation of 5-lipoxygenase which is involved in leukotriene production [36]. Interestingly, 5-lipoxygenase has been implicated in aging and neurodegenerative diseases [37], as well as other psychiatric disorders [38], including anxiety and depression, which are frequently co-morbid conditions of autism. Collectively, the involvement of these specific genes that are associated with neurological function and disease and their presence in pathways regulated by inflammatory mediators lend further support to the neural inflammation model for autism.

In addition to the possible role of genes involved in inflammation, a review of the gene list in Table 3 suggests several additional recurring themes among the differentially expressed genes with neurological functions: neuronal survival, neurite extension/guidance, and myelination. In this regard, altered expression of EGR2 may be particularly significant. EGR2 (Krox-20) is a transcription factor involved in the development of the brain and peripheral nervous system, routing of axons, and myelination [39]. Some of these functions may be related to EGR2-mediated regulation of ROBO1, which is involved in neuronal differentiation and axon guidance [40, 41], and integrin beta-7 (ITGB7) which has been implicated in chronic demyelinating disease [42]. The expression levels of all three of these genes are relatively reduced with increased severity of autism or language impairment. The involvement of cell migration and survival in the pathophysiology of autism is also implicated by the higher expression level of CHL1, a novel neural cell adhesion molecule that is involved in neurite migration, outgrowth, connectivity, and survival, which is associated with the more autistic phenotype. Deficiency in CHL1 has been shown to be associated with mental and motor impairments as well as with alterations in exploratory and emotional behavior in mice [43, 44], characteristics that are often associated with autism. However, the effect of CHL1 overexpression has yet to be determined. While the function of such neurologically relevant genes in lymphoblastoid cell lines is unknown, if expression of these genes can be shown to be consistently altered in LCL, these cells, and by inference their precursor blood lymphocytes, can potentially be used as reporter cells for diagnosis of ASD.

The observed relationship between differential gene expression and severity of ASD between monozygotic twins suggests a role for epigenetic factors in ASD. Indeed, epigenetic differences between monozygotic twins have been examined as possible causes for discordancy in schizophrenia as well as bipolar disorder [46-48]. A recent report on normal monozygotic twins indicates that epigenetic differences arise over time, increasing with age and with separation from each other after birth [45]. Possible epigenetic mechanisms leading to differences in gene expression include differential methylation, differences in histone acetylation, and micro RNA, although there is no available evidence linking any of these to autism at this time. On the other hand, a mutation in a methyl-CpG binding protein, X-linked MeCP2, has been identified as being involved in 80% of all cases of Rett Syndrome, a developmental disorder which overlaps ASD, thus implicating the importance of methylation-dependent gene expression in at least this related disorder. One could therefore postulate that differential methylation or differential histone acetylation might give rise to differential expression in LCL from monozygotic twins with ASD and test for global changes in methylation or histone acetylation as done by Fraga et al [45]. If present, these differences could, in turn, be the result of stochastic processes, environmental factors, or the immortalization procedure used to generate cell lines from primary lymphocytes. The latter possibility could be further tested by evaluation of the methylation/acetylation patterns of DNA/histones in primary lymphocytes from monozygotic twins discordant in severity of autism or language impairment within autism which, while interesting, is outside of the scope of this study. Regardless of origin, the gene expression differences between monozygotic twins who present with differential severity along the autism spectrum or within a specific domain (eg., language) are potentially useful, not only as biomarkers for ASD, but also as indicators of genes or metabolic/signaling pathways that may contribute to the autistic phenotype. While our short list of candidate genes focuses on genes that are similarly differentially expressed between twin sets, the set of differentially expressed, neurologically relevant genes that are unique to a given twin set may also be important to the determination of a specific autistic phenotype. Inasmuch as our microarray analyses directly compared genetically matched individuals who differ only in degree of expression of autistic symptoms, it is likely that other genes, not identified in our study, also play a role in the etiology and pathophysiology of autism. This experimental design possibly explains why the candidate genes identified here are different from those reported by an earlier genomic study [20] which compared autopsy brain tissues from autistic and normal (nonautistic) controls (i.e., case-control studies). On the other hand, it is interesting that many of our novel genes map to genetically identified autism susceptibility loci or QTLs (Table 7 and Supplementary Table 1).

Aside from identifying novel candidate genes for autism, our study also demonstrates the need for phenotype definition or subgrouping according to severity along a specific behavioral domain for biological studies of autism. Specifically, the results show that the differential gene expression profiles of concordantly autistic twins with differential severity of language impairment mirror some of the differences in gene expression which are observed in the twins with discordant diagnosis of autism, who also exhibit differential language deficits. Thus, for case-control studies in which individuals from the general population are compared against unrelated controls, subgrouping the autistic individuals by phenotype or stratifying them according to severity of symptoms may provide more clarity in analyzing biological data. Towards this goal, we have used several different clustering methods to divide over 1300 autistic individuals into endophenotypic subgroups (eg., language, nonverbal communication, and savant skills) based on item scores on the ADIR questionnaire (manuscript in preparation). Based on these methods, the twin siblings analyzed in this study each fall into different clusters in all but one case involving a discordant twin set. These "endophenotypic" differences may therefore account for some of the differences in gene expression profiles between the siblings as well as among the different sets of twins.

CONCLUSIONS

In summary, this data indicates that LCL from genetically identical autistic individuals who differ in severity of autistic symptoms and/or language impairment exhibit differential expression of genes relevant to neurological development, structure, and function. Many of these genes map to regions previously identified by genetic analyses as harboring autism susceptibility genes or QTLs, demonstrating the power of combined genomic-genetic analyses to prioritize autism candidate genes for further study. In addition, a quantitative relationship is seen between severity of symptoms and expression of several autism candidate genes when twins with classic autism or with milder autistic traits are compared against their respective normal siblings. The finding that gene expression differences were also observed in cells from twins who were both diagnosed as autistic, but who differed in severity in language deficits strongly suggests that autistic phenotype as well as severity of symptoms must be considered in gene expression studies on autistic individuals in order to reduce biological heterogeneity due to these factors. Collectively, these studies provide proof-of-principle that LCL (or peripheral blood cells) may exhibit biomarkers relevant to autism, and further suggest their potential usefulness as reporter cells in developing a diagnostic screen for autism. While it is unlikely that microarray studies on LCL will identify the etiology(ies) of autism, this global approach to gene expression is expected to highlight molecular or pathway defects related to the pathophysiology of the condition which can be targeted for drug therapies. Moreover, as opposed to fixed autopsy tissues in which RNA may have degraded, a live cell model can be used to examine the functional consequences of the genomic alteration(s) and the efficacy of different pharmacological agents in ameliorating the impaired function.

Materials and Methods

Cell Lines and Culture Conditions

Lymphoblastoid cell lines (LCL) derived from lymphocytes of 5 pairs of monozygotic twins with ASD were obtained from the Autism Genetic Resource Exchange (AGRE; Los Angeles, Calif.) and cultured in DMEM with 15% fetal bovine serum and 1% penicillin-streptomycin. Cell lines from normal siblings of 2 sets of twins were also obtained for comparison of gene expression profile with that of their respective autistic siblings. In addition, cell lines from a set of non-autistic monozygotic twins were also studied. To minimize differences in gene expression due to culture and sample workup conditions, all samples that underwent direct comparison of gene expression profile were cultured and harvested at the same time using the same medium preparation and RNA isolation reagents.

Description of Individual Donors of Cell Lines

Supplementary Table 2 provides a case description of all of the subjects included in this study. In brief, all of the twin pairs and normal siblings, with the exception of 1 set of twins, were Caucasian males between the ages of 6 and 16 at the time that blood was drawn. The remaining set of twins (age 12) was of mixed race (black, Hispanic) but had the same mother as one of the Caucasian pairs of autistic twins. For 3 sets of twins (designated "discordant" twins), one twin of each pair met standard diagnostic criteria for autism based on the Autism Diagnostic Interview-Revised (ADIR) [13]. In each case, his co-twin, while not clinically autistic, exhibited autistic traits and could be considered to be on the autism spectrum. These co-twins were described either as "Broad spectrum" or "Not quite autistic (NQA)" by the AGRE repository according to criteria established on the basis of ADI-R scores. Gene expression in cell lines from two of these twin pairs were also directly compared against the gene expression profile in cell lines from their respective "normal" sibling. Two of the 5 sets of twins with ASD (designated "concordant" twins) were examples in which both co-twins were diagnosed with autism, but who were discordant in severity of language impairment, as indicated by their respective percentile scores on the Peabody Picture Vocabulary Test (PPVT). The Autism Diagnostic Observation Schedule (ADOS) [14] was used to diagnose one of these sets of twins. None of the individuals whose cells were used presented with any co-morbid condition or mental retardation. All of the phenotypic data were obtained through the AGRE databases (www.agre.org).

DNA Microarray Analyses

RNA was isolated from the LCL using TRIzol Reagent (Invitrogen, CA) according to the manufacturer's protocol. The RNA was further purified using Centricon-X columns and tested for purity on RNA 6000 NanoChips using the Agilent 2100 Bioanalyzer. Labeled cDNA was obtained by incorporation of 5-(3-aminoallyl)-2' deoxyuridine-5'-triphosphate (Ambion, Tex.) during first-strand synthesis, followed by coupling to the ester of cyanine (Cy)-3 or Cy-5 (Molecular Probes, OR) as appropriate according to Standard Operating Protocol (SOP) M004 on The Institute for Genomic Research (TIGR) website (http://www.tigr.org). For two-color microarray analyses, the Cy5- and Cy3 labeled cDNA from each pair of twins (or twin and normal sib) were co-hybridized using TIGR SOP M005 to spotted microarrays (TIGR 40K Human Set) containing 39,936 human cDNA probes which were obtained from Research Genetics. Dye reversal (flip-dye) replicates were included in all analyses, and at least 2 sets of replicates were carried out for each pair of monozygotic twins. Gene expression levels were derived from the scanned hybridized arrays using TIGR SpotFinder; MIDAS, and MeV analysis programs which are all part of the TM4 Microarray Analysis Software Package available at the above-cited website. These programs have all been previously described in detail [49]. Data analyses included normalization using local LOWESS followed by standard deviation regularization across individual subarrays, and flip-dye consistency checking for dye reversal replicates as implemented in MIDAS [50, 51]. The SAM (Significance analysis of microarrays) module within MeV was used to determine statistical significance of differential expression and false discovery rates (FDR) for genes from biological replicates.

Quantitative RT-PCR

Total RNA was reverse transcribed into cDNA using the iScript cDNA Synthesis Kit (Bio-Rad, Hercules, Calif.). Briefly, 2 µg of RNA were added to a 40 µl reaction mix containing reaction buffer, magnesium chloride, dNTPs, an optimized blend of random primers and oligo(dT), an RNase inhibitor, and a MMLV RNase H+ reverse transcriptase. The reaction was incubated at 25° C. for 5 minutes followed by 42° C. for 30 minutes and ending with 85° C. for 5 minutes. The cDNA reactions were then diluted to a volume of 100 µl with water. Real-time PCR was carried out on a 7900HT Sequence Detection System from Applied Biosystems using the iTaq SYBR Green Supermix with ROX (Bio-Rad, Hercules, Calif.). Gene-specific primers at a final concentration of 200 nM and 1 µl of cDNA templates were combined into 20 µl reaction mixes and run through 40 cycles of PCR. Quantitation was performed using the Universal 18S rRNA primers (Ambion, Austin, Tex.) with samples normalized to their 18S rRNA standard curves. Forward and reverse primers are described in Supplementary Table 3.

Network Prediction Analyses

Lists of differentially expressed genes identified as "significant" by the 1-sample t-test on microarray data across different sets of twins were analyzed using Ingenuity Pathways Analysis (Ingenuity Systems, Inc.), a web-delivered application that enables biologists to discover, visualize and explore therapeutically relevant networks significant to their specific experimental results (e.g., gene expression array data sets). Specifically, a data set containing gene identifiers (in this case, GenBank Accessions) and their corresponding expression values were uploaded as an Excel spreadsheet using the template provided in the application. Each gene identifier was mapped to its corresponding gene object in the Ingenuity Pathways Knowledge Base. The gene list was filtered prior to analysis with Ingenuity by using a log 2 cutoff of 0.58. These genes were then used as the starting point for generating biological networks. The networks are displayed graphically as nodes (genes/gene products) and edges (the biological relationships between the nodes). Human, mouse, and rat orthologs of a gene are stored as separate objects in the knowledge base, but are represented as a single node in the network. The intensity of the node color indicates the degree of up-(red) or down-(green) regulation. When networks from different samples are merged, yellow node color denotes overlapping differentially expressed genes from two or more samples. Nodes are displayed using various shapes that represent the functional class of the gene product. (See Ingenuity's website [http://www.ingenuity.com] for shape legend)

Global Functional Analyses

Biological functions were assigned to the overall analysis (across data from 5 monozygotic twin pairs) by using the findings that have been extracted from the scientific literature and stored in the Ingenuity Pathways Knowledge Base. The biological functions assigned to the analysis are ranked according to the significance of that biological function to the analysis. A Fisher's exact test is used to calculate a p-value determining the probability that the biological function assigned to the analysis is explained by chance alone.

in Silico Mapping of Differentially Expressed Genes

The physical locations of each of the significant differentially expressed genes with log 2 ratio ≥±0.58 were obtained using TIGR's Resourcerer Gene Annotation Software. These locations were then compared manually to those of autism candidate genes (ACG) or quantitative trait loci (QTLs) identified on the basis of genetic linkage and association studies.

Systems for Analysis of Arrays

In an embodiment, the present invention provides systems for carrying out array analysis. Thus, in an embodiment, the present invention comprises a computer-readable medium on which is encoded programming code for analyzing gene expression from a plurality of data points comprising a gene list which is filtered using a log 2 cutoff of 0.58.

Also in an embodiment, the present invention may comprise a computer-readable medium on which is encoded programming code for analyzing gene expression comprising code for: (a) determining cross-correlation between at least two genes within a group, wherein cross-correlation indicates a gene involved with neuronal development and function.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, VISUAL C#®, VISUAL BASIC®, VISUAL FOXPRO®, Java, and JavaScript.

As described above, the system may comprise an imaging unit as well as a means for the user to interact with the system as the analysis proceeds. Thus, in an embodiment, the present invention further comprises a unit for collecting and/or compiling data from said plurality of measured signals and transmitting said data to said computer, and a unit for transmitting the results of said analysis to a user.

REFERENCES

1. American Psychiatric Association, American Psychiatric Association. Task Force on DSM-IV: Diagnostic and statistical manual of mental disorders: DSM-IV, 4th edn. Washington, D.C.: American Psychiatric Association; 1994.
2. Crino P B, Henske E P: New developments in the neurobiology of the tuberous sclerosis complex. *Neurology* 1999, 53(7):1384-1390.
3. Bolton P F: Neuroepileptic correlates of autistic symptomatology in tuberous sclerosis. *MentRetard Dev Disabil Res Rev* 2004, 10(2): 126-131.
4. Temudo T, Maciel P: [Rett's syndrome. Clinical features and advances in genetics]. *Rev Neurol* 2002, 34 Suppl 1:S54-58.
5. Hansen R S, Gartler S M, Scott C R, Chen S H, Laird C D: Methylation analysis of CGG sites in the CpG island of the human FMR1 gene. *Hum Mol Genet* 1992, 1(8):571-578.
6. Gedeon A K, Baker E, Robinson H, Partington M W, Gross B, Manca A, Korn B, Poustka A, Yu S, Sutherland G R et al: Fragile X syndrome without CCG amplification has an FMR1 deletion. *Nat Genet* 1992, 1(5):341-344.
7. Identification and characterization of the tuberous sclerosis gene on chromosome 16. The European Chromosome 16 Tuberous Sclerosis Consortium. *Cell* 1993, 75(7):1305-1315.
8. Henske E P, Ozelius L, Gusella J F, Haines J L, Kwiatkowski D J: A high-resolution linkage map of human 9q34.1. *Genomics* 1993, 17(3):587-591.
9. Kandt R S: Tuberous sclerosis: the next step. *J Child Neurol* 1993, 8(2):107-110; discussion 110-101.
10. Kandt R S, Haines J L, Smith M, Northrup H, Gardner R J, Short M P, Dumars K, Roach E S, Steingold S, Wall S et al: Linkage of an important gene locus for tuberous sclerosis to a chromosome 16 marker for polycystic kidney disease. *Nat Genet* 1992, 2(1):37-41.
11. Mulley J C, Sutherland G R: Integrating maps of chromosome 16. *Curr Opin Genet Dev* 1993, 3(3):425-431.
12. van Slegtenhorst M, de Hoogt R, Hermans C, Nellist M, Janssen B, Verhoef S, Lindhout D, van den Ouweland A, Halley D, Young J et al: Identification of the tuberous sclerosis gene TSC1 on chromosome 9q34. *Science* 1997, 277(5327):805-808.
13. Lord C, Rutter M, Le Couteur A: Autism Diagnostic Interview-Revised: a revised version of a diagnostic interview for caregivers of individuals with possible pervasive developmental disorders. *J Autism Dev Disord* 1994, 24(5):659-685.
14. Lord C, Rutter M, Goode S, Heemsbergen J, Jordan H, Mawhood L, Schopler E: Autism diagnostic observation schedule: a standardized observation of communicative and social behavior. *J Autism Dev Disord* 1989, 19(2):185-212.
15. Yonan A L, Palmer A A, Smith K C, Feldman I, Lee H K, Yonan J M, Fischer S G, Pavlidis P, Gilliam T C: Bioinformatic analysis of autism positional candidate genes using biological databases and computational gene network prediction. *Genes Brain Behav* 2003, 2(5):303-320.
16. Geschwind D H: DNA microarrays: translation of the genome from laboratory to clinic. *Lancet Neurol* 2003, 2(5):275-282.
17. Schena M, Shalon D, Davis R W, Brown P O: Quantitative monitoring of gene expression patterns with a complementary DNA microarray. *Science* 1995, 270(5235):467-470.
18. Lipshutz R J, Fodor S P, Gingeras T R, Lockhart D J: High density synthetic oligonucleotide arrays. *Nat Genet* 1999, 21(1 Suppl):20-24.
19. Pongrac J, Middleton F A, Lewis D A, Levitt P, Mimics K: Gene expression profiling with DNA microarrays: advancing our understanding of psychiatric disorders. *Neurochem Res* 2002, 27(10):1049-1063.
20. Purcell A E, Jeon O H, Zimmerman A W, Blue M E, Pevsner J: Postmortem brain abnormalities of the glutamate neurotransmitter system in autism. *Neurology* 2001, 57(9):1618-1628.
21. Morley M, Molony C M, Weber T M, Devlin J L, Ewens K G, Spielman R S, Cheung V G: Genetic analysis of genome-wide variation in human gene expression. *Nature* 2004, 430(7001):743-747.
22. Sharma A, Sharma V K, Horn-Saban S, Lancet D, Ramachandran S, Brahmachari S K: Assessing natural variations in gene expression in humans by comparing with monozygotic twins using microarrays. *Physiol Genomics* 2005, 21(1):117-123.
23. Kakiuchi C, Iwamoto K, Ishiwata M, Bundo M, Kasahara T, Kusumi I, Tsujita T, Okazaki Y, Nanko S, Kunugi H et al: Impaired feedback regulation of XBP1 as a genetic risk factor for bipolar disorder. *Nat Genet* 2003, 35(2):171-175.
24. Mak Y T, Hampson G, Beresford J N, Spector T D: Variations in genome-wide gene expression in identical twins—a study of primary osteoblast-like culture from female twins discordant for osteoporosis. *BMC Genet* 2004, 5(1):14.
25. Iwamoto K, Kakiuchi C, Bundo M, Ikeda K, Kato T: Molecular characterization of bipolar disorder by comparing gene expression profiles of postmortem brains of major mental disorders. *Mol Psychiatry* 2004, 9(4):406-416.
26. Kato T, Iwayama Y, Kakiuchi C, Iwamoto K, Yamada K, Minabe Y, Nakamura K, Mori N, Fujii K, Nanko S et al: Gene expression and association analyses of LIM (PD-LIM5) in bipolar disorder and schizophrenia. *Mol Psychiatry* 2005.

27. Coutinho A M, Oliveira G, Morgadinho T, Fesel C, Macedo T R, Bento C, Marques C, Ataide A, Miguel T, Borges L et al: Variants of the serotonin transporter gene (SLC6A4) significantly contribute to hyperserotonemia in autism. *Mol Psychiatry* 2004, 9(3):264-271.
28. Bradley S L, Dodelzon K, Sandhu H K, Philibert R A: Relationship of serotonin transporter gene polymorphisms and haplotypes to mRNA transcription. Am J Med Genet B Neuropsychiatr Genet 2005, 136(1):58-61.
29. Lesch K P, Bengel D, Heils A, Sabol S Z, Greenberg B D, Petri S, Benjamin J, Muller C R, Hamer D H, Murphy D L: Association of anxiety-related traits with a polymorphism in the serotonin transporter gene regulatory region. *Science* 1996, 274(5292):1527-1531.
30. Hattori Y, Campbell E B, Gross S S: Argininosuccinate synthetase mRNA and activity are induced by immunostimulants in vascular smooth muscle. Role in the regeneration or arginine for nitric oxide synthesis. *J Biol Chem* 1994, 269(13):9405-9408.
31. Akyol O, Zoroglu S S, Armutcu F, Sahin S, Gurel A: Nitric oxide as a physiopathological factor in neuropsychiatric disorders. In Vivo 2004, 18(3):377-390.
32. Heneka M T, Schmidlin A, Wiesinger H: Induction of argininosuccinate synthetase in rat brain glial cells after striatal microinjection of immunostimulants. *J Cereb Blood Flow Metab* 1999, 19(8):898-907.
33. Vargas D L, Nascimbene C, Krishnan C, Zimmerman A W, Pardo C A: Neuroglial activation and neuroinflammation in the brain of patients with autism. *Ann Neurol* 2005, 57(1):67-81.
34. Wang W J, Kuo J C, Yao C C, Chen R H: DAP-kinase induces apoptosis by suppressing integrin activity and disrupting matrix survival signals. *J Cell Biol* 2002, 159(1): 169-179.
35. Gupta S: A decision between life and death during TNF-alpha-induced signaling. *J Clin Immunol* 2002, 22(4):185-194.
36. Byrum R S, Goulet J L, Griffiths R J, Koller B H: Role of the 5-lipoxygenase-activating protein (FLAP) in murine acute inflammatory responses. *J Exp Med* 1997, 185(6): 1065-1075.
37. Manev H, Uz T, Sugaya K, Qu T: Putative role of neuronal 5-lipoxygenase in an aging brain. *Faseb J* 2000, 14(10): 1464-1469.
38. Manev R, Manev H: 5-Lipoxygenase as a putative link between cardiovascular and psychiatric disorders. *Crit. Rev Neurobiol* 2004, 16(1-2):181-186.
39. Kamholz J, Awatramani R, Menichella D, Jiang H, Xu W, Shy M: Regulation of myelinspecific gene expression. Relevance to CMT1. *Ann NY Acad Sci* 1999, 883:91-108.
40. Connor R M, Key B: Expression and role of Roundabout-1 in embryonic *Xenopus forebrain*. *Dev Dyn* 2002, 225(1):22-34.
41. Lee J S, Ray R, Chien C B: Cloning and expression of three zebrafish roundabout homologs suggest roles in axon guidance and cell migration. *Dev Dyn* 2001, 221(2):216-230.
42. Kanwar J R, Harrison J E, Wang D, Leung E, Mueller W, Wagner N, Krissansen G W: Beta7 integrins contribute to demyelinating disease of the central nervous system. *J Neuroimmunol* 2000, 103(2):146-152.
43. Buhusi M, Midkiff B R, Gates A M, Richter M, Schachner M, Maness P F: Close homolog of L1 is an enhancer of integrin-mediated cell migration. *J Biol Chem* 2003, 278(27):25024-25031.
44. Naus S, Richter M, Wildeboer D, Moss M, Schachner M, Bartsch J W: Ectodomain shedding of the neural recognition molecule CHL1 by the metalloprotease-disintegrin ADAM8 promotes neurite outgrowth and suppresses neuronal cell death. *J Biol Chem* 2004, 279(16):16083-16090.
45. Fraga M F, Ballestar E, Paz M F, Ropero S, Setien F, Ballestar M L, Heine-Suner D, Cigudosa J C, Urioste M, Benitez J et al: Epigenetic differences arise during the lifetime of monozygotic twins. *Proc Natl Acad Sci USA* 2005, 102(30):10604-10609.
46. Abdolmaleky H M, Thiagalingam S, Wilcox M: Genetics and epigenetics in major psychiatric disorders: dilemmas, achievements, applications, and future scope. *Am J Pharmacogenomics* 2005, 5(3):149-160.
47. Petronis A, Gottesman, I I, Kan P, Kennedy J L, Basile V S, Paterson A D, Popendikyte V: Monozygotic twins exhibit numerous epigenetic differences: clues to twin discordance? *Schizophr Bull* 2003, 29(1):169-178.
48. Petronis A: Epigenetics and bipolar disorder: new opportunities and challenges. *Am J Med Genet C Semin Med Genet* 2003, 123(1):65-75.
49. Saeed A I, Sharov V, White J, Li J, Liang W, Bhagabati N, Braisted J, Klapa M, Currier T, Thiagarajan M et al: TM4: a free, open-source system for microarray data management and analysis. *Biotechniques* 2003, 34(2):374-378.
50. Yang I V, Chen E, Hasseman J P, Liang W, Frank B C, Wang S, Sharov V, Saeed A I, White J, Li J et al: Within the fold: assessing differential expression measures and reproducibility in microarray assays. *Genome Biol* 2002, 3(11):research0062.
51. Quackenbush J: Microarray data normalization and transformation. *Nat Genet* 2002, 32 Suppl:496-501.
52. Alarcon M, Yonan A L, Gilliam T C, Cantor R M, Geschwind D H: Quantitative genome scan and Ordered-Subsets Analysis of autism endophenotypes support language QTLs. *Mol Psychiatry* 2005, 10(8):747-757.
53. Robinson P D, Schutz C K, Macciardi F, White B N, Holden J J: Genetically determined low maternal serum dopamine beta-hydroxylase levels and the etiology of autism spectrum disorders. *Am J Med Genet* 2001, 100(1): 30-36.
54. A genomewide screen for autism: strong evidence for linkage to chromosomes 2q, 7q, and 16p. *Am J Hum Genet* 2001, 69(3):570-581.
55. Persico A M, D'Agruma L, Maiorano N, Totaro A, Militerni R, Bravaccio C, Wassink T H, Schneider C, Melmed R, Trillo S et al: Reelin gene alleles and haplotypes as a factor predisposing to autistic disorder. *Mol Psychiatry* 2001, 6(2):150-159.
56. Chen G K, Kono N, Geschwind D H, Cantor R M: Quantitative trait locus analysis of nonverbal communication in autism spectrum disorder. *Mol Psychiatry* 2005.
57. Bradford Y, Haines J, Hutcheson H, Gardiner M, Braun T, Sheffield V, Cassayant T, Huang W, Wang K, Vieland V et al: Incorporating language phenotypes strengthens evidence of linkage to autism. *Am J Med Genet* 2001, 105(6): 539-547.
58. Veenstra-VanderWeele J, Kim S J, Lord C, Courchesne R, Akshoomoff N, Leventhal B L, Courchesne E, Cook E H, Jr.: Transmission disequilibrium studies of the serotonin 5-HT2A receptor gene (HTR2A) in autism. *Am J Med Genet* 2002, 114(3):277-283.
59. Vervoort V S, Beachem M A, Edwards P S, Ladd S, Miller K E, de Mollerat X, Clarkson K, DuPont B, Schwartz C E, Stevenson R E et al: AGTR2 mutations in X-linked mental retardation. *Science* 2002, 296(5577):2401-2403.
60. Wassink T H, Brzustowicz L M, Bartlett C W, Szatmari P: The search for autism disease genes. *Ment Retard Dev Disabil Res Rev* 2004, 10(4):272-283.

61. Serajee F J, Nabi R, Zhong H, Mahbubul Huq A H: Association of INPP1, PIK3CG, and TSC2 gene variants with autistic disorder: implications for phosphatidylinositol signalling in autism. *J Med Genet* 2003, 40(11):e119.
62. Cantor R M, Kono N, Duvall J A, Alvarez-Retuerto A, Stone J L, Alarcon M, Nelson S F, Geschwind D H: Replication of autism linkage: fine-mapping peak at 17q21. *Am J Hum Genet* 2005, 76(6):1050-1056.
63. Bacchelli E, Blasi F, Biondolillo M, Lamb J A, Bonora E, Barnby G, Parr J, Beyer K S, Klauck S M, Poustka A et al: Screening of nine candidate genes for autism on chromosome 2q reveals rare nonsynonymous variants in the cAMP-GEFII gene. *Mol Psychiatry* 2003, 8(11):916-924.
64. Philippe A, Martinez M, Guilloud-Bataille M, Gillberg C, Rastam M, Sponheim E, Coleman M, Zappella M, Aschauer H, Van Maldergem L et al: Genome-wide scan for autism susceptibility genes. Paris Autism Research International Sibpair Study. *Hum Mol Genet* 1999, 8(5): 805-812.
65. Serajee F J, Zhong H, Nabi R, Huq A H: The metabotropic glutamate receptor 8 gene at 7q31: partial duplication and possible association with autism. *J Med Genet* 2003, 40(4): e42.
66. Wassink T H, Piven J, Vieland V J, Huang J, Swiderski R E, Pietila J, Braun T, Beck G, Folstein S E, Haines J L et al: Evidence supporting WNT2 as an autism susceptibility gene. *Am J Med Genet* 2001, 105(5):406-413.
67. Jamain S, Quach H, Betancur C, Rastam M, Colineaux C, Gillberg I C, Soderstrom H, Giros B, Leboyer M, Gillberg C et al: Mutations of the X-linked genes encoding neuroligins NLGN3 and NLGN4 are associated with autism. *Nat Genet* 2003, 34(1):27-29.
68. Lamb J A, Barnby G, Bonora E, Sykes N, Bacchelli E, Blasi F, Maestrini E, Broxholme J, Tzenova J, Weeks D et al: Analysis of IMGSAC autism susceptibility loci: evidence for sex limited and parent of origin specific effects. *J Med Genet* 2005, 42(2):132-137.

These references are incorporated herein in their entirety, particularly as they relate to teaching the level of ordinary skill in this art and for any disclosure necessary for the commoner understanding of the subject matter of the invention as defined by the claims.

It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

TABLE 1

Significant up- and down-regulated genes from SAM analysis of microarray experiments on 3 sets of monozygotic twins discordant for autism diagnosis with log2(ratio) ≥ ± 0.58

| Genbank # | Gene name or description | Mean log2(ratlo)* | Obs. d score$^\Delta$ | qPCR$^\yen$ |
|---|---|---|---|---|
| | Upregulated (log2(ratio) ≥ 0.58) | | | |
| R45254 | Unknown protein, | 1.19 | 2.95 | |
| AA448599 | F13A1, clotting factor XIIIa precursor | 1.08 | 2.26 | |
| AA676466 | ASS, argininosuccinate synthetase (aa 1-412) | 0.92 | 5.92 | |
| AA992985 | Unknown protein | 0.88 | 2.38 | |
| AA676405 | ASS, argininosuccinate synthetase (aa 1-412) | 0.85 | 4.56 | 1.47 |
| W07099 | NAGLU, N-acetylglucosaminidase, alpha | 0.85 | 2.24 | −0.28 |
| AA044267 | P2X5a | 0.80 | 2.36 | |
| T49652 | FLAP, ALOX5AP | 0.79 | 1.88 | 1.01 |
| H57830 | histone H1(0) (aa 1-194) | 0.78 | 4.53 | |
| R00276 | CD38 alt | 0.76 | 1.45 | |
| AA488070 | Unknown protein | 0.75 | 1.63 | |
| W69399 | histone H1(0) (aa 1-194) | 0.74 | 7.15 | |
| H09567 | PAG1 | 0.74 | 1.97 | |
| AA609189 | Unknown protein | 0.73 | 1.87 | |
| H02307 | FLAP, ALOX5AP | 0.70 | 1.79 | |
| N50114 | PAG1 | 0.69 | 2.30 | |
| Al091671 | Unknown protein | 0.67 | 2.14 | |
| N70181 | PLEKHG1 | 0.66 | 2.85 | |
| H24011 | Homeodomain-like protein | 0.64 | 1.66 | |
| AA412520 | Unknown protein | 0.63 | 1.97 | |
| AA521362 | CR2 receptor | 0.62 | 1.80 | |
| Al371096 | DAPK1, death-associated protein kinase 1 | 0.62 | 1.58 | 0.65 |
| T61343 | IL6ST, IL6 signal traríducer, gp130 | 0.59 | 1.91 | 0.58 |
| N29918 | ZBTB10 | 0.59 | 1.55 | |
| T90067 | EIF2C2 | 0.59 | 3.24 | |
| | Downregulated (log2(ratio) ≤ −0.58) | | | |
| T67053 | IGLC2 | −2.39 | −5.93 | |
| W73790 | IGLL1 | −2.00 | −8.34 | |
| H18423 | Unknown protein | −1.98 | −8.42 | |
| AA448157 | CYP1B1 | −0.95 | −2.38 | |
| AA644099 | Unknown protein | −0.89 | −1.73 | |
| AA933744 | ECAT11 | −0.84 | −1.97 | |
| Al018127 | Unknown protein | −0.83 | −2.26 | |
| AA451886 | CYP1B1 | −0.77 | −2.90 | |
| AA682565 | Unknown protein from neuroblastoma | −0.72 | −3.06 | |
| Al223429 | Unknown protein | −0.69 | −2.37 | |
| AA450353 | ELMOD1 | −0.69 | −1.87 | |
| AA873578 | IGHG1 | −0.67 | −2.29 | |
| R33402 | SAMSN1 | −0.67 | −1.92 | |
| AA173755 | ROBO1, roundabout 1 | −0.66 | −3.00 | −0.93 |
| AA022886 | retinal degeneration B beta | −0.64 | −2.70 | |

TABLE 1-continued

Significant up- and down-regulated genes from SAM analysis of microarray experiments on 3 sets of monozygotic twins discordant for autism diagnosis with log2(ratio) ≥± 0.58

| Genbank # | Gene name or description | Mean log2(ratio)* | Obs. d score^Δ | qPCR^¥ |
|---|---|---|---|---|
| AA063573 | SAMSN1 | −0.64 | −1.74 | |
| H99699 | mitochondrial aconitase | −0.63 | −2.79 | |
| AI290663 | CYBASC3 | −0.60 | −3.20 | |
| AA449333 | Rab22b | −0.58 | −1.71 | |

* Mean log$_2$(ratio) of gene expression in lymphoblastoid cell lines from children exhibiting classic autism to cell lines from less affected monozygotic twin sibs.
^Δ Observed d score from SAM analysis for which median FDR was 26.4%.
^¥ Mean log$_2$(ratio) of qPCR data from 3 sets of monozygotic twins. Each gene was analyzed in triplicate and the mean log$_2$(ratio) for each respective gene was averaged among the 3 sets. Only one gene, NAGLU, was not confirmed by qPCR, possibly because of suboptimal choice of primers for qPCR.
Genes in boldface type have been shown to be relevant to neurological development, structure, or function (See Table 3).

TABLE 2

Expression of ASS, CHL1, and FLAP in 2 sets of discordant monozygotic twins relative to expression levels in their respective normal siblings

| Gene name | Genbank # | A1 | | M1 | | A2 | | M2 | |
|---|---|---|---|---|---|---|---|---|---|
| ASS | AA676405 | 0.65 | (0.81)* | −0.13 | (0.27) | 1.77 | (3.04) | 0.18 | (0.97) |
| CHL1 | H15267 | 1.60 | (1.64) | 0.67 | (1.39) | 1.15 | (0.78) | 0.95 | (0.60) |
| FLAP | T49652 | 0.71 | (1.10) | 0.13 | (0.77) | 1.40 | (1.45) | −0.09 | (−0.39) |

Values are mean log$_2$(ratio) measures of gene expression between a twin and his respective normal sibling, obtained by DNA microarray analyses with dye reversal replicates
* Values in parentheses are mean log$_2$(ratio) measures obtained by triplicate qPCR analyses.
A = autistic twin as diagnosed by ADI-R scoresheet
M = more mildly affected twin who did not meet ADI-R criteria for autism

TABLE 3

Network focus genes from Ingenuity Pathways Analysis with log$_2$(ratio) >± 0.58

| GenBank # | Gene | Neurological function or disease |
|---|---|---|
| Upregulated | | |
| T49652 | ALOX5AP | neuronal signaling; possibly neurodegenerative diseases |
| AA991590 | APOC1 | |
| AA147170 | ALS4 | ataxia-ocular apraxia |
| AA676466 | ASS | involved in nitric oxide production |
| H21041 | ATF3 | extension of neurites |
| AA702350 | AUTS2 | Asperger's syndrome |
| AI341427 | BCAT1 | |
| AA430367 | CBS | |
| R00276 | CD38 | |
| AA283949 | CDC14A | |
| N67039 | CDK6 | |
| H15267 | CHL1 | extension of neurites; organization of mossy fibers |
| AA521362 | CR2 | |
| AA884403 | CTF1 | myelination, differentiation of neurons |
| AI371096 | DAPKI | apoptosis of hippocampal neurons |
| W00789 | DST | coalignment of neurofilaments, projection of axons; dysmyelination |
| AA448599 | F13A1 | stroke |
| AA149640 | FLT1 | VEGF-induced release of nitric oxide |
| AA070902 | GGA2 | |
| AI375302 | HMGB1 | extension of neurites |
| AI539460 | IL7 | |
| AA406546 | IL6ST | myelination, development of motor neurons, retraction of dendrites |
| H09062 | MLSTD1 | |
| W07099 | NAGLU | neurogenesis; vacuolation of neurons |
| AA598611 | NR4A2 | neurogenesis; metabolism of dopamine |
| AA707195 | NTRK2 | survival of Purkinje cells; apoptosis of neurons |
| AA044267 | P2RX5 | |
| H09567 | PAG | possible role in chronic neuroinflammation |
| AA972337 | PAWR | |
| AA489629 | PBEF1 | |
| AI016039 | PLXNB2 | |
| R80217 | PTGS2 | activation of astrocytes; spatial memory in mice; apoptosis of neurons |
| AA495950 | RRM2B | |
| R27457 | SLC38A2 | |

TABLE 3-continued

Network focus genes from Ingenuity Pathways Analysis with log$_2$(ratio) >± 0.58

| GenBank # | Gene | Neurological function or disease |
|---|---|---|
| AI091460 | SOS1 | |
| N63153 | SPRED1 | |
| AI040821 | TERE1 | |
| AA970358 | TSLP | |
| Downregulated | | |
| AA779727 | ADAM19 | development of septum |
| R01732 | AMPD3 | |
| AA478589 | APOE | quantity/morphology of neurons; neurite extension; learning in mice |
| AA984646 | C7orf2 | |
| AA448157 | CYP1B1 | |
| AA446027 | EGR2 | myelination; development of motor neurons; routing of axons |
| AA149096 | HCK | |
| AA620511 | HSPA8 | |
| W73790 | IGLL1 | |
| AI380522 | ITGB7 | chronic demyelinating disease |
| AA679503 | KIF1B | morphology and size of brain; neuron survival |
| AA029283 | LARGE | |
| T83159 | LSP1 | |
| AI351740 | LTB | neurological disorder in rats |
| AA022886 | PITPNC1 | |
| AI126054 | PTK2 | |
| AA173755 | ROBO1 | axon guidance |
| AA457700 | SCD | neural regeneration |
| AA504211 | TNFSF11 | |
| N68465 | UAP1 | |

Dataset included genes derived from SAM test across three twin sets that met expression cutoff in at least one of the twin sets.
Genes in Boldfaced type are ones of neurological relevance.

TABLE 4

Relative expression of candidate genes in monozygotic "concordant" twin pairs with differential language impairment (PPVT percentile scores) and in normal twins

| Candidate Gene | Genbank # | PPVT-30/42* | | PPVT-0.1/1 | | Discordant twins¥ | | Normal twins | |
|---|---|---|---|---|---|---|---|---|---|
| ASS | AA676405 | 0.03 | (−0.26)¶ | −0.01 | (−0.69) | 0.85 | (1.37) | 0.24 | (0.54) |
| CHL1 | H15267 | 1.83 | (1.48) | 1.99 | (1.29) | 0.61 | (0.46) | 1.40 | (1.45) |
| IL6ST | T61343 | 0.88 | (1.33) | 0.28 | (−0.26) | 0.58 | (0.49) | 0.37 | (0.23) |
| IL6ST | AA406546 | 1.02 | (0.85) | 0.34 | (−0.14) | 0.58 | (0.61) | 0.43 | (0.47) |
| DAPK1 | AI371096 | −0.56 | (−0.92) | −0.49 | (−1.05) | 0.70 | (0.57) | −0.13 | (−0.18) |
| FLAP | T49652 | 1.18 | (1.20) | 0.28 | (−0.25) | 0.71 | (0.58) | −0.19 | (−0.34) |
| ITGB7 | AI380522 | −1.12 | (−1.13) | −0.20 | (−0.92) | −0.60 | (−0.76) | 0.15 | (0.04) |
| EGR2 | AA446027 | −2.02 | (−3.10) | −1.26 | (−2.16) | −0.43 | (−0.79) | −0.23 | (−0.37) |
| ROBO1 | AA173755 | −0.13 | (0.25) | 0.41 | (−0.18) | −0.66 | (−1.10) | −0.45 | (−0.80) |
| 5-HTT¶ | BC069484 | NP¶ | (−2.39) | NP | (−0.42) | NP | (−0.96) | NP | (−0.02) |

*Values are mean log2 ratios of gene expression from DNA microarray data from 2 sets of monozygotic autistic twins who both met criteria for autism by either ADOS or ADI-R diagnostic tests, but have differential language impairment as indicated by their respective PPVT percentile scores. Data from 2 separate dye-reversal microarray experiments were averaged for each twin set. For each pair of twins, microarray data from the twin with the lower PPVT score was used as the numerator in calculating the gene expression ratio. PPVT-30/42 refers to the twin pair whose PPVT percentile scores are 30 and 42, while PPVT-0.1/1 refers to the twin pair whose percentile scores are 0.1 and 1. Interestingly, the two sets of twins share the same mother. The PPVT-30/42 set are Caucasian males, as are the 3 sets of discordant twins, while the more severely language-impaired twins (PPVT-0.1/1) are black, Latino males.
Values in parentheses are mean log$_2$(ratio) expression measures obtained by triplicate qPCR analyses.
¥Mean expression value across 3 sets of twins discordant for diagnosis of classic autism.
¶Not present (NP) on microarray

TABLE 5

Significant genes with mean log$_2$(ratio) ≥ 0.58 across 5 sets of twins with ASD

| Genbank # | Gene name or description | Mean log$_2$ (ratio)* | Obs. d score$^\Delta$ |
|---|---|---|---|
| | Unregulated (log2(ratio) ≥ 0.58) | | |
| AA448599 | F13A1, clottin,g factor XIIIa precursor | 1.50 | 3.15 |
| H15267 | CHL1, neural cell adhesion molecule | 1.10 | 2.82 |
| AA521362 | CR2 receptor | 1.07 | 2.21 |
| R00276 | CD38 alt | 0.83 | 2.10 |
| W07099 | NAGLU, N-acetylglucosaminidase, alpha | 0.77 | 3.77 |
| T49652 | FLAP, ALOX5AP | 0.77 | 2.85 |
| AA044267 | P2X5a | 0.76 | 3.22 |
| R40400 | CHL1, neural cell adhesion molecule | 0.75 | 2.25 |
| H09567 | PAG1 | 0.71 | 2.64 |
| AI400399 | CYP7B1 | 0.70 | 2.01 |

TABLE 5-continued

Significant genes with mean $\log_2$(ratio) ≥ 0.58 across 5 sets of twins with ASD

| Genbank # | Gene name or description | Mean $\log_2$ (ratio)* | Obs. d score$^\Delta$ |
|---|---|---|---|
| AA149640 | FLT1 | 0.67 | 3.61 |
| H17800 | Unknown protein | 0.67 | 3.06 |
| H02307 | FLAP, ALOX5AP | 0.67 | 2.71 |
| AA917693 | Unknown protein | 0.66 | 2.64 |
| Al017382 | ATXN7L1 | 0.66 | 1.95 |
| Al391671 | Unknown protein | 0.65 | 2.74 |
| N50114 | PAG1 | 0.65 | 2.82 |
| H95977 | Nmd protein, PLA1A | 0.65 | 1.97 |
| AA040389 | Unknown protein | 0.64 | 2.58 |
| H24011 | Homeodomain-like protein | 0.64 | 2.71 |
| Al275120 | Unknown protein | 0.63 | 2.59 |
| AA708955 | SCHIP1, schwannomin interacting protein 1 | 0.62 | 2.07 |
| AA406546 | IL6ST, IL6 signal transducer, gp130 | 0.62 | 3.19 |
| R79082 | PTPRK | 0.59 | 2.24 |
| Al241341 | CHL1, neural cell adhesion molecule | 0.59 | 2.41 |
| T61343 | IL6ST, IL6 signal transducer, gp130 | 0.59 | 3.07 |
| Downregulated ($\log_2$(ratio) ≤ −0.58) | | | |
| AA446027 | EGR2, Krox-20 homolog | −0.90 | −2.41 |
| AA630734 | seryl-tRNA synthetase | −0.86 | −2.15 |
| R47893 | CCL3L1 | −0.80 | −2.14 |
| AA682565 | Unknown protein from neuroblastoma | −0.76 | −3.03 |
| R78530 | COTL1 | −0.73 | −2.55 |
| AA933744 | ECAT11 | −0.73 | −2.52 |
| N58443 | GPR55 | −0.68 | −3.04 |
| H99699 | mitochondrial aconitase | −0.64 | −4.86 |
| H03494 | CD44 | −0.63 | −2.42 |
| AA450353 | ELMOD1 | −0.63 | −2.86 |
| AA458965 | IL32, natural killer cell protein, transcript 4 | −0.63 | −2.87 |
| R33402 | SAMSNI | −0.62 | −3.29 |
| AA111969 | CD83 antigen | −0.60 | −2.55 |
| Al380522 | ITGB7, integrin beta-7 subunit | −0.60 | −2.51 |
| AA682637 | CHST2 | −0.59 | −2.85 |

\* Mean $\log_2$(ratio) of gene expression across 5 sets of twins with ASD. SAM analysis revealed 1281 significant genes with a median FDR of 15.6%.
Genes in boldface type have been shown to be relevant to neurological development, structure, or function.

TABLE 6

Global Functional Analysis: Enrichment of high level functions represented in datasets of differentially expressed genes across 5 sets of monozygotic twins

| High Level Function | Twin Sets | | | | |
|---|---|---|---|---|---|
| | 361/360 Significance* | 809/810 Significance | 2369/2363 Significance | 2596/2596 Significance | 2597/2595 Significance |
| Nervous system development and function | 0.008-3.85 × 10$^{-2}$ | 0.12-2.55 × 10$^{-2}$ | 0.81-4.79 × 10$^{-2}$ | 0.12-4.39 × 10$^{-2}$ | 0.02-1.53 × 10$^{-2}$ |
| Tissue morphology | 0.008-4.27 × 10$^{-2}$ | NA | 0.81-4.79 × 10$^{-2}$ | 0.08-4.38 × 10$^{-2}$ | 0.51-4.03 × 10$^{-2}$ |
| Cell death | 0.01-4.27 × 10$^{-2}$ | 3.74 × 10$^{-2}$ | 0.09-4.79 × 10$^{-2}$ | 0.18-4.65 × 10$^{-2}$ | 0.09-4.53 × 10$^{-2}$ |
| Cellular development | 0.01-4.27 × 10$^{-2}$ | NA | 0.81-4.79 × 10$^{-2}$ | 0.12-4.30 × 10$^{-2}$ | 0.03-3.54 × 10$^{-2}$ |
| Immune and lymphatic system development and function | 0.03-3.85 × 10$^{-2}$ | NA | 0.81-4.79 × 10$^{-2}$ | 0.33-4.39 × 10$^{-2}$ | 0.19-4.03 × 10$^{-2}$ |

Global functional analysis of differential gene expression across 5 sets of monozygotic autistic twins (identified by blood satanic numbers (eg., 361/360) who are discordant with respect to severity of autism or language impairment was performed using Ingenuity's Pathways Analysis Software.
*Significance calculated for each function is an indicator of the likelihood that the high level function is associated with the dataset by random chance. The p-value, which is calculated using the right-tsiled Fisher's Exact Test, compares the number of user-specified genes of interest (in this case, differentially expressed genes with a $\log_2$(ratio) cutoff ≥± 0.58) that participate in a given function or pathway to the total number of occurrances of these genes in all functional/pathway annotations stored in the Ingenuity Pathways Knowledge Base. It is noteworthy that genes related to nervous system development and function rank first among the top 5 out of 74 high level functions identified in lymphoblastoid cell lines on the basis of differentially expressed genes across 5 sets of twins with autism spectrum disorders. The range of significance values for each high level function relates to the different significance values for specific subfunctions within the category.
NA: no significance value for this function

TABLE 7

Differentially expressed candidate genes from microarray experiments mapped in silica to autism susceptibility genes and QTL.

| Candidate gene | Genebank # | Physical location | Reported closely mapped autism candidate genes or QTL* | Rotl |
|---|---|---|---|---|
| ASS | AA676405 | chr9 (130,349,882-130,406,214) | dopamine beta-hydroxylase (9q34) | 53 |
| CHL1 | H15267 | chr9 (423,533-426,095) | KIAA0121 (3p25.2) | 54 |
| IL6R-beta, go130 | T61343 | chr5(55,267,950-55,272,765) | Spoken language QTL chr5:40(0-67) | 52 |
| IL6ST | AA406546 | chr5 (55,271,809-55,272,305) | Spoken language QTL chr5:40(0-67) | 52 |
| DAPK1 | Al371096 | chr9 (87,552,642-37,553,099) | | |
| FLAP, ALOX5AP | T49552 | chr13 (30,207,643-30,236,932) | AUTS3 (13q14-22). HTR2A-2 (serobnin rocco. 2A) (13q14-21) | 57,58 |
| ITGB7 | Al380522 | chr12 (51,871,361-51,887,333) | arginine vasopressin receptor IA (12q14-15) | 60 |
| EGR2 | AA446027 | chr10 (64,241,755-64,246,031) | Spoken language QTL chr10:107(72-126); HTR-7 | 52 |
| ROBO1 | AA173755 | chr3 (76,729,082-78,729,496) | | |

SUPPLEMENTARY TABLE 2

Case description of subjects from whom LCL were derived and used in this study.

| Individual ID | Blood ID | Ethnicity | Zygosity | Age* | Status | PPVT (% Ile) | Raven |
|---|---|---|---|---|---|---|---|
| AU002704 | HI0361 | Caucasian | MZ | 8 | Autism | | 108 |
| AU002703 | HI0360 | Caucasian | MZ | 8 | Br. Spec. | 79 (8) | 105 |
| AU057904 | HI0609 | Caucasian | MZ | 6 | Autism | 35 (0.1) | 83 |
| AU057905 | HI0810 | Caucasian | MZ | 6 | Br. Spec. | 117 (87) | 110 |
| AU057903 | HI0813 | Caucasian | | 10 | nonautistic | | |
| AU0885303 | HI2369 | Caucasian | MZ | 16 | Autism | No data | No data |
| AU0885302 | HI2368 | Caticasian | MZ | 16 | NQA | " | " |
| AU0885304 | HI2357 | Caucasian | | 19 | nonautistic | " | " |
| AU0616301 | HI2595 | Caucasian | MZ | 15 | Autism¥ | 92 (30) | 104 |
| AU0616302 | HI2596 | Caucasian | MZ | 15 | Autism¥ | 97 (42) | 94 |
| AU0616303 | HI2597 | Mixed, Hispanic | MZ | 12 | Autism | 40 (<0.1) | 80 |
| AU0616304 | HI2598 | Mixed, Hispanic | MZ | 12 | Autism | 66 (1) | 107 |
| AU1165305 | HI2745 | Caucasian | MZ | 9 | nonautistic | | |
| AU1165306 | HI2744 | Caucasian | MZ | 9 | nonautistic | | |

*Age at time of inclusion in study
¥Diagnosed with ADOS rather than ADIR

SUPPLEMENTARY TABLE 3

Primers used for quantitative RT-PCR analyses

| Gene Name | GenBank # | Forward Primer (5' to 3') | Reverse Primer (5' to 3') |
|---|---|---|---|
| ASS | AA676405 | GAAGTGCGCAAAATCAAACA | CTGCACTTTCCCTTCCACTC |
| CHL1 | H15627 | TTTAGATGCACCCGTGTTTG | AGCACACCAACATTTCTCATT |
| DAPK1 | AI371096 | CGCTACCTCTCTGTCCCTTG | AGGATTCCCTTCTCCCCTTT |
| EGR2 | AA446027 | CCCATCACAGGTTTTTGACC | TCTTTTTGCTGTCCCCACTT |
| FLAP | T49652 | GACGATCTCCACCACCATCT | AGAATGCTCTCAAGAGCTGAA |
| IL6ST | T61343 | TTAAAAGGTGGCAGCTCAGG | TCATCACACGACCCATCAAC |
| IL6ST | AA406546 | GCTGGGCTCATGTAGTTATGG | CATCAGAGTGGCTTAGGGACA |
| ITCB7 | AI380522 | CATCACGACCACCATCAATC | CTCCAGTTCCCACTGTCCTC |
| NAGLU | W07099 | TCCAACAGCACCAGTTTGAC | AGCCGGGGTAATATTTGAGG |
| NAGLU | W07099 | ACACTCCGGAGCAGTAGCC | AAAGGACCCAGTGCCAGATT |
| ROBO1 | AA173755 | CTGACCCCAGTGGAAAACA | CCCTTAGTACTGCACGCCTTT |
| 5-HTT | BC069484 | CCTCCAGCCACTTATTTCCA | ACCTCCATCCACATCCTCAC |
| Control Primers | | | |
| MLC1 | AA196486 | TGAAGAGCTGAATGCCAAGA | CCTTGTCAAAGACACGCAGA |
| TCRb | AA909476 | CATGAGCATCAGCCTTCTGT | GAAAGGCCTGTCCACTCTCC |
| Werner HIP | AA189052 | GGCTATGGCAAAGGCTACAA | GAGTCAGCACCTCCTCTGCT |

Forward primer sequence identifiers from top to bottom: SEQ ID NOS: 1, 3, 5, 7, 9 11, 13, 15, 17, 19, 21, 23, 25, 27, 29.

Reverse primer sequences identifiers from top to bottom are: SEQ ID NOS: 2, 4, 6, 8, 10, 12, 14, 16, 18, 20, 22, 24, 26, 28, 30.

What is claimed is:

1. A composition comprising:
an ensemble consisting of nucleic acid molecules produced from a sample of peripheral blood cells of an individual having autism hybridized to a nucleic acid molecule probe spatially arrayed and affixed to a solid surface for each of argininosuccinate synthetase (ASS), interleukin-6 signal transducer (IL6ST), death-associated protein kinase 1 (DAPK1), 5-lipoxygenase activating protein (FLAP (ALOX5AP)), and Roundabout homolog 1 precursor (ROBO1), wherein each of the nucleic acid molecules produced from the sample contain a label that is capable of emitting a detectable signal.

2. A composition comprising
an ensemble consisting of nucleic acid molecules produced from a sample of peripheral blood cells of an individual having autism hybridized to nucleic acid molecule probe spatially arrayed and affixed to a solid surface for each of argininosuccinate synthetase (ASS) interleukin-6 signal transducer (IL6ST), death-associated protein kinase (DAPK1), 5-lipoxygenase activating protein (FLAP (ALOX5AP), Roundabout homolog 1 precursor (ROBO1), and
at least one of integrin beta-7LCL: lymphoblastoid cell lines (ITGB7), cell adhesion molecule with homology to L1CAM (CHL1), and 5-hydroxytryptamine (serotonin) transporter (5-HTT)), wherein each of the nucleic acid molecules produced from the sample contain a label that is capable of emitting a detectable signal.

3. The composition of claim 1, wherein the sample of peripheral blood cells comprises white blood cells or their lymphoblast derivatives.

4. The composition of claim 2, wherein the sample of peripheral blood cells comprises white blood cells or their lymphoblast derivatives.

5. The composition of claim 1, wherein each of the probes contains from about 15 to about 25 nucleotides.

6. The composition of claim 1, wherein the label is fluorescent.

7. An array consisting of nucleic acid probes for each of argininosuccinate synthetase (ASS), interleukin-6 signal transducer (IL6ST), death-associated protein kinase (DAPK1), 5-lipoxygenase activating protein (FLAP (ALOX5AP)), and Roundabout homolog precursor (ROBO1), wherein the probes are spatially arrayed and affixed to a solid surface.

8. The array of claim 7, wherein each of the probes are from about 15 to about 25 nucleotides in size.

9. The array of claim 7, wherein at least one of the probes is bound to a nucleic acid molecule to form a complex, wherein the complex emits a detectable signal.

10. The array of claim 9, wherein the detectable signal is fluorescent.

* * * * *

```
                        SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
gaagtgcgca aaatcaaaca                                           20

<210> SEQ ID NO 2
<211> LENGTH: 20
```

```
<212> TYPE: DNA
<213> ORGANISM: Artificial Sequence
<220> FEATURE:
<223> OTHER INFORMATION: PCR Primer

<400> SEQUENCE: 2
ctgcactttc ccttccactc                                               20

<210> SEQ ID NO 3
<211> LENGTH: 20
<212> TYPE: DNA
<213> ORGANISM: Artificial Sequence
<220> FEATURE:
<223> OTHER INFORMATION: PCR Primer

<400> SEQUENCE: 3
tttagatgca cccgtgtttg                                               20

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
agcacaccaa catttctcat t                                             21

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
cgctacctct ctgtcccttg                                               20

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
aggattccct tctccccttt                                               20

<210> SEQ ID NO 7
<211> LENGTH: 20
<212> TYPE: DNA
<213> ORGANISM: Artificial Sequence
<220> FEATURE:
<223> OTHER INFORMATION: PCR Primer

<400> SEQUENCE: 7
cccatcacag gttttttgacc                                              20

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
``` tcttttgct gtccccactt                                            20

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gacgatctcc accaccatct                                           20

<210> SEQ ID NO 10
<211> LENGTH: 21
<212> TYPE: DNA
<213> ORGANISM: Artificial Sequence
<220> FEATURE:
<223> OTHER INFORMATION: PCR Primer

<400> SEQUENCE: 10
agaatgctct caagagctga a                                         21

<210> SEQ ID NO 11
<211> LENGTH: 20
<212> TYPE: DNA
<213> ORGANISM: Artificial Sequence
<220> FEATURE:
<223> OTHER INFORMATION: PCR Primer

<400> SEQUENCE: 11
ttaaaaggtg gcagctcagg                                           20

<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12
tcatcacacg acccatcaac                                           20

<210> SEQ ID NO 13
<211> LENGTH: 21
<212> TYPE: DNA
<213> ORGANISM: Artificial Sequence
<220> FEATURE:
<223> OTHER INFORMATION: PCR Primer

<400> SEQUENCE: 13
gctgggctca tgtagttatg g                                         21

<210> SEQ ID NO 14
<211> LENGTH: 21
<212> TYPE: DNA
<213> ORGANISM: Artificial Sequence
<220> FEATURE:
<223> OTHER INFORMATION: PCR Primer

<400> SEQUENCE: 14
catcagagtg gcttagggac a                                         21

<210> SEQ ID NO 15
<211> LENGTH: 20
<212> TYPE: DNA
<213> ORGANISM: Artificial Sequence -continued

```
<220> FEATURE:
<223> OTHER INFORMATION: PCR Primer

<400> SEQUENCE: 15
catcacgacc accatcaatc                                                    20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
ctccagttcc cactgtcctc                                                    20

<210> SEQ ID NO 17
<211> LENGTH: 20
<212> TYPE: DNA
<213> ORGANISM: Artificial Sequence
<220> FEATURE:
<223> OTHER INFORMATION: PCR Primer

<400> SEQUENCE: 17
tccaacagca ccagtttgac                                                    20

<210> SEQ ID NO 18
<211> LENGTH: 20
<212> TYPE: DNA
<213> ORGANISM: Artificial Sequence
<220> FEATURE:
<223> OTHER INFORMATION: PCR Primer

<400> SEQUENCE: 18
agccggggta atatttgagg                                                    20

<210> SEQ ID NO 19
<211> LENGTH: 19
<212> TYPE: DNA
<213> ORGANISM: Artificial Sequence
<220> FEATURE:
<223> OTHER INFORMATION: PCR Primer

<400> SEQUENCE: 19
acactccgga gcagtagcc                                                     19

<210> SEQ ID NO 20
<211> LENGTH: 20
<212> TYPE: DNA
<213> ORGANISM: Artificial Sequence
<220> FEATURE:
<223> OTHER INFORMATION: PCR Primer

<400> SEQUENCE: 20
aaaggaccca gtgccagatt                                                    20

<210> SEQ ID NO 21
<211> LENGTH: 19
<212> TYPE: DNA
<213> ORGANISM: Artificial Sequence
<220> FEATURE:
<223> OTHER INFORMATION: PCR Primer

<400> SEQUENCE: 21
ctgaccccag tggaaaaca                                                     19
```

<210> SEQ ID NO 22
<211> LENGTH: 21
<212> TYPE: DNA
<213> ORGANISM: Artificial Sequence
<220> FEATURE:
<223> OTHER INFORMATION: PCR Primer

<400> SEQUENCE: 22
cccttagtac tgcacgcctt t                                              21

<210> SEQ ID NO 23
<211> LENGTH: 20
<212> TYPE: DNA
<213> ORGANISM: Artificial Sequence
<220> FEATURE:
<223> OTHER INFORMATION: PCR Primer

<400> SEQUENCE: 23
cctccagcca cttatttcca                                                20

<210> SEQ ID NO 24
<211> LENGTH: 20
<212> TYPE: DNA
<213> ORGANISM: Artificial Sequence
<220> FEATURE:
<223> OTHER INFORMATION: PCR Primer

<400> SEQUENCE: 24
acctccatcc acatcctcac                                                20

<210> SEQ ID NO 25
<211> LENGTH: 20
<212> TYPE: DNA
<213> ORGANISM: Artificial Sequence
<220> FEATURE:
<223> OTHER INFORMATION: PCR Primer

<400> SEQUENCE: 25
tgaagagctg aatgccaaga                                                20

<210> SEQ ID NO 26
<211> LENGTH: 20
<212> TYPE: DNA
<213> ORGANISM: Artificial Sequence
<220> FEATURE:
<223> OTHER INFORMATION: PCR Primer

<400> SEQUENCE: 26
ccttgtcaaa gacacgcaga                                                20

<210> SEQ ID NO 27
<211> LENGTH: 20
<212> TYPE: DNA
<213> ORGANISM: Artificial Sequence
<220> FEATURE:
<223> OTHER INFORMATION: PCR Primer

<400> SEQUENCE: 27
catgagcatc agccttctgt                                                20

<210> SEQ ID NO 28
<211> LENGTH: 20
<212> TYPE: DNA
<213> ORGANISM: Artificial Sequence
<220> FEATURE:
<223> OTHER INFORMATION: PCR Primer

```
<400> SEQUENCE: 28
gaaaggcctg tccactctcc                                               20

<210> SEQ ID NO 29
<211> LENGTH: 20
<212> TYPE: DNA
<213> ORGANISM: Artificial Sequence
<220> FEATURE:
<223> OTHER INFORMATION: PCR Primer

<400> SEQUENCE: 29
ggctatggca aaggctacaa                                               20

<210> SEQ ID NO 30
<211> LENGTH: 20
<212> TYPE: DNA
<213> ORGANISM: Artificial Sequence
<220> FEATURE:
<223> OTHER INFORMATION: PCR Primer

<400> SEQUENCE: 30
gagtcagcac ctcctctgct                                               20
```